United States Patent
Hayase et al.

[11] Patent Number: 6,004,952
[45] Date of Patent: Dec. 21, 1999

[54] MICACOCIDIN DERIVATIVES

[75] Inventors: Yoshio Hayase, Mie; Shinobu Kobayashi, Shiga; Kazuo Ueda, Mie; Shigetada Hidaka, Shiga, all of Japan

[73] Assignee: Shinogi & Co., Ltd., Osaka, Japan

[21] Appl. No.: 09/117,734

[22] PCT Filed: Feb. 4, 1997

[86] PCT No.: PCT/JP97/00266

§ 371 Date: Aug. 5, 1998

§ 102(e) Date: Aug. 5, 1998

[87] PCT Pub. No.: WO97/29096

PCT Pub. Date: Aug. 14, 1997

[30] Foreign Application Priority Data

Feb. 5, 1996 [JP] Japan ................................ 8-044243

[51] Int. Cl.$^6$ .................... C07D 277/10; A01K 31/425
[52] U.S. Cl. ...................... 514/184; 514/365; 548/101; 548/104; 548/146
[58] Field of Search .................... 548/101, 104, 548/146; 514/184, 365

[56] References Cited

U.S. PATENT DOCUMENTS 5,707,838  1/1998  Takeda .................................... 435/118

*Primary Examiner*—Robert Gerstl
*Attorney, Agent, or Firm*—Foley & Lardner

[57] ABSTRACT

The object of the present invention is to provide a novel compound which has various biological activities and is useful for medical and animal drugs. The present invention provides a compound represented by the formula:

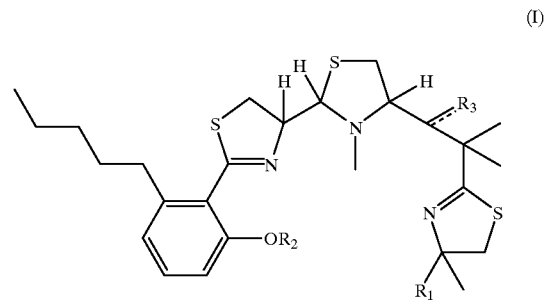

(I)

wherein $R^1$ is $COOR^4$, $CONR^5R^6$, $CO-R^7-OR$ or $CH_2OR^8$; $R^2$ is hydrogen atom, alkyl, aralkyl, heteroaryl, heteroarylalkyl, $COR^{13}$, $COOR^{14}$, $CONR^{15}R^{16}$; $R^3$ is hydrogen atom or $OR^3$; a broken line ( - - - ) represents the presence of a double bond when $R^3$ is oxygen atom and the absence of a double bond when $R^3$ is $OR^3$, or a salt or metal chelete thereof.

12 Claims, No Drawings

MICACOCIDIN DERIVATIVES

DETAILED DESCRIPTION OF THE INVENTION

FIELD OF THE INVENTION

The present invention relates to a novel compound useful in the field of medicine and veterinary medicine, and to medical and animal drugs containing said compound.

BACKGROUND OF THE INVENTION

Pyochelin, which is produced by Pseudomonas aeruginosa, is known as a compound having a similar structure to that of the present invention (J. Bacteriology 137(1), 357, 1979). However, it is unknown whether it has also a biological activity similar to that of the compound of the present invention.

Subject of the Invention to be Solved

The object of the present invention is to provide a novel compound having various biological activities useful for medical and animal drugs.

Means for Solving the Subject

The present inventors have made extended studies to attain the object mentioned above and have found that a novel compound of the formula (I) shown below has antimycoplasma activity, anti-coccidium activity, antibacterial activity, antifungal activity and immunosuppressive activity.

Thus, the present invention provides a compound of the formula (I):

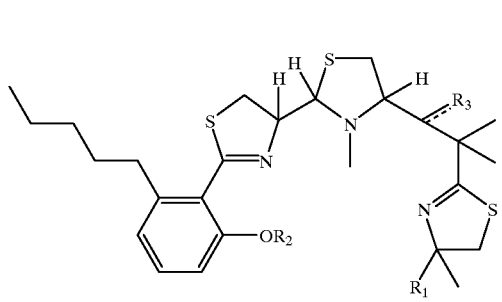

(I)

wherein $R^1$ is (1) $COOR^4$ wherein $R^4$ is hydrogen atom, optionally substituted alkyl, optionally substituted aralkyl, optionally substituted heteroaryl or optionally substituted heteroarylalkyl; (2) $CONR^5R^6$ wherein $R^5$ and $R^6$ are the same or different and represent hydrogen atom, hydroxyl, optionally substituted alkyl, optionally substituted alkoxyl, optionally substituted aryl, optionally substituted aralkyl, optionally substituted heteroaryl or optionally substituted heteroarylalkyl, provided that when one of $R^5$ and $R^6$ is hydroxyl or optionally substituted alkoxyl, the other is hydrogen atom, optionally substituted alkyl, optionally substituted aryl or optionally substituted aralkyl; (3) CO—$R^7$—OR wherein $R^7$ is α-amino acid residue and R is hydrogen atom or alkyl; or (4) $CH_2OR^8$ wherein $R^8$ is hydrogen atom, optionally substituted alkyl, optionally substituted aralkyl, optionally substituted heteroaryl, optionally substituted heteroarylalkyl, $COR^9$ wherein $R^9$ is hydrogen atom, optionally substituted alkyl, optionally substituted aryl, optionally substituted aralkyl, optionally substituted heteroaryl or optionally substituted heteroarylalkyl, $COOR^{10}$ wherein $R^{10}$ is optionally substituted alkyl, optionally substituted aryl, optionally substituted aralkyl, optionally substituted heteroaryl or optionally substituted heteroarylalkyl, or $CONR^{11}R^{12}$ wherein $R^{11}$ and $R^{12}$ are the same or different and represent hydrogen atom, optionally substituted alkyl, optionally substituted aryl, optionally substituted aralkyl, optionally substituted heteroaryl or optionally substituted heteroarylalkyl;

$R^2$ is hydrogen atom, optionally substituted alkyl, optionally substituted aralkyl, optionally substituted heteroaryl, optionally substituted heteroarylalkyl, $COR^{13}$ wherein $R^{13}$ is hydrogen atom, optionally substituted alkyl, optionally substituted aryl, optionally substituted aralkyl, optionally substituted heteroaryl or optionally substituted heteroarylalkyl, $COOR^{14}$ wherein $R^{14}$ is optionally substituted alkyl, optionally substituted aryl, optionally substituted aralkyl, optionally substituted heteroaryl or optionally substituted heteroarylalkyl, or $CONR^{15}R^{16}$ wherein $R^{15}$ and $R^{16}$ are the same or different and represent hydrogen atom, optionally substituted alkyl, optionally substituted aryl, optionally substituted aralkyl, optionally substituted heteroaryl or optionally substituted heteroarylalkyl;

a broken line ( - - - ) represents the presence or absence of a double bond, provided that when it presents the presence of the double bond, $R^3$ is oxygen atom, or when it represents the absence of the double bond, $R^3$ is $OR^{3'}$ wherein $R^{3'}$ is hydrogen atom, optionally substituted alkyl, optionally substituted aralkyl, optionally substituted heteroaryl, optionally substituted heteroarylalkyl, $COR^{17}$ wherein $R^{17}$ is hydrogen atom, optionally substituted alkyl, optionally substituted aryl, optionally substituted aralkyl, optionally substituted heteroaryl or optionally substituted heteroarylalkyl, $COOR^{18}$ wherein $R^{18}$ is optionally substituted alkyl, optionally substituted aryl, optionally substituted aralkyl, optionally substituted heteroaryl or optionally substituted heteroarylalkyl, or $CONR^{19}R^{20}$ wherein $R^{19}$ and $R^{20}$ are the same or different and represent hydrogen atom, optionally substituted alkyl, optionally substituted aryl, optionally substituted aralkyl, optionally substituted heteroaryl or optionally substituted heteroarylalkyl, or a salt or metal chelate thereof, provided that the metal chelate is excluded when $R^1$ is COOH, $R^2$ is hydrogen atom, and $R^3$ is OH.

An optionally substituted alkyl represented by $R^2$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{3'}$ includes $C_1$–$C_{10}$ alkyl, preferably $C_1$–$C_4$ alkyl, specifically methyl, ethyl, propyl, isopropyl, n-butyl, isobutyl, sec-butyl, tert-butyl and the like, preferably methyl, ethyl and propyl, and especially preferably methyl.

When these alkyls are substituted, the substituents include halogen atom (for example, fluorine, chlorine, bromine and iodine); $C_1$–$C_5$ alkoxy, preferably $C_1$–$C_3$ alkoxy (for example, methoxy, ethoxy and propoxy); $C_1$–$C_5$ alkylthio, preferably $C_1$–$C_3$ alkylthio, for example, methylthio, ethylthio or propylthio; alkoxycarbonyl having $C_1$–$C_5$ alkoxyl, preferably $C_1$–$C_3$ alkoxyl, for example, methoxycarbonyl, ethoxycarbonyl, propoxycarbonyl or the like; carboxy; hydroxy; hydroxy; amino which is optionally substituted with $C_1$–$C_5$ alkyl or alkanoyl, preferably $C_1$–$C_3$ alkyl or alkanoyl, for example, amino, monomethyl amino, dimethyl amino, acethyl amino or the like; or $C_1$–$C_3$ alkanoyloxy, for example, acetoxyl or the like, preferably halogen atom, alkoxy or hydroxy, and particularly chlorine, fluorine, methoxy, ethoxy or hydroxy is preferred.

These substitutents can bind to said alkyl at any possible position, and the number of the substituents is preferably one to three, more preferably one to two.

An optionally substituted aralkyl represented by $R^2$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{3'}$ includes for example benzyl, phenethyl, (α- or β-) naphthyl methyl and the like. Possible substituents on the aralkyl group include halogen atom, for example, fluorine, chlorine, bromine or iodine; $C_1$–$C_5$ alkyl, preferably $C_1$–$C_3$ alkyl, for example, methyl, ethyl, propyl and the like; $C_1$–$C_5$ alkoxy, preferably $C_1$–$C_3$ alkoxy, for example, methoxy, ethoxy, propoxy and the like; $C_1$–$C_5$ alkyl halide, preferably $C_1$–$C_3$ alkyl halide, for example, fluoromethyl, dichloromethyl, difluoromethyl, trifluoromethyl, fluoroethyl, dichloroethyl and the like; nitro; cyano and so on. These substitutents may bind to any possible position on the aralkyl group, and the number of the substituents is preferably one to three, more preferably one to two.

An optionally substituted heteroaryl represented by $R^2$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{3'}$ include the heteroaryl containing in its ring one or more oxygen atoms, sulfur atoms or nitrogen atoms arbitrarily selected, for example, pyridyl, pyrimidinyl, furyl, thienyl, pyrrolyl, quinolyl, oxazolyl, isoxazolyl, indolyl and the like. The heteroaryl may be optionally substituted, by halogen atom, for example, fluorine, chlorine, bromine or iodine atom; $C_1$–$C_5$ alkyl, preferably $C_1$–$C_3$ alkyl, for example, methyl, ethyl, propyl and the like; $C_1$–$C_5$ alkoxy, preferably $C_1$–$C_3$ alkoxy, for example, methoxy, ethoxy, propoxy and the like; $C_1$–$C_5$ alkyl halide, preferably $C_1$–$C_3$ alkyl halide, for example, fluoromethyl, dichloromethyl, difluoromethyl, trifluoromethyl, fluoroethyl, dichloroethyl and the like; nitro; cyano and so on. These substitutents may bind to any possible position on the heteroaryl ring, and the number of the substituents is preferably one to three, more preferably one to two. The heteroaryl may further be fused with other heteroaryl or carbon ring.

Examples of optionally substituted heteroarylalkyls represented by $R^2$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{3'}$ include those which are composed of the heteroaryl mentioned above and $C_1$–$C_5$ alkyl, preferably $C_1$–$C_2$ alkyl, for example, methyl, ethyl or the like. Specific examples are picolyl, pyridylethyl, thenyl, fulfuryl and the like. The heteroarylalkyls may be substituted by similar substitutents to those aforementioned for the heteroaryl group.

An optionally substituted alkoxy represented by $R^5$ and $R^6$ includes $C_1$–$C_5$ alkoxy, preferably $C_1$–$C_3$ alkoxy, and specific examples are methoxy, ethoxy, propoxy, isopropoxy and the like. The alkoxy may be substituted by halogen atom, for example, fluorine, chlorine, bromine and iodine atom; $C_1$–$C_5$ alkoxy, preferably $C_1$–$C_3$ alkoxy, such as methoxy, ethoxy, propoxy and the like; and optionally substituted phenyl, such as chlorophenyl, tolyl, methoxyphenyl, nitrophenyl, and the like. These substitutents may bind to any possible position on the alkoxy group, and the number of the substituents is preferably one to three, more preferably one to two.

Examples of the optionally substituted aryl represented by $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ include $C_6$–$C_{14}$ aryl, preferably $C_6$–$C_{10}$ aryl. Specific examples are phenyl, α-naphthyl, β-naphthyl and the like. The aryl is optionally substituted by a halogen atom, for example, fluorine, chlorine, bromine and iodine; $C_1$–$C_5$ alkyl, preferably $C_1$–$C_3$ alkyl, for example, methyl, ethyl, propyl and the like; $C_1$–$C_5$ alkoxy, preferably $C_1$–$C_3$ alkoxy, for example, methoxy, ethoxy, propoxy and the like; $C_1$–$C_5$ alkyl halide, preferably $C_1$–$C_3$ alkyl halide, for example, fluoromethyl, dichloromethyl, difluoromethyl, trifluoromethyl, fluoroethyl, dichloroethyl and the like; nitro; cyano and the like.

These substitutents may bind to any possible position of said aryl, and the number of the subusitituents is preferably one to three, more preferably one to two.

An α-amino acid residue represented by $R^7$ includes cysteine (Cys) residue, glycine (Gly) residue, serine (Ser) residue, alanine (Ala) residue and the like.

An alkyl represented by R includes the same groups as those exemplified as the alkyl groups of the optionally substituted alkyl represented by $R^2$ or the like stated above.

$R^1$ is preferably the groups represented by $COOR^4$ wherein $R^4$ is preferably hydrogen, optionally substituted alkyl or optionally substituted benzyl, or $CONR^5R$ wherein $R^5$ and $R^6$ are independently preferably hydrogen atom, hydroxy, alkoxy, alkyl, carboxyalkyl, alkoxycarbonylalkyl or hydroxyalkyl. More preferably, $R^1$ is carboxy, alkoxycarbonyl, alkoxyalkoxycarbonyl, hydroxyalkoxycarbonyl, benzyloxycarbonyl, benzyloxycarbonyl halide, carbamoyl, monoalkylcarbamoyl, dialkylcarbamoyl, hydroxycarbamoyl, N-alkylhydroxycarbamoyl, carboxyalkylcarbamoyl or alkoxycarbonylalkylcarbamoyl.

$R^2$ is preferably hydrogen atom, optionally substituted alkyl, optionally substituted benzyl or optionally substituted alkanoyl. More preferably, $R^2$ is hydrogen atom, alkyl, alkoxyalkyl, alkyl halide, benzyl halide, or alkanoyl.

$R^3$ is preferably oxygen atom or a group represented by $OR^{3'}$ wherein $R^{3'}$ is preferably hydrogen atom, optionally substituted alkyl, optionally substituted benzyl or optionally substituted alkanoyl. More preferably, $R^3$ is oxygen atom, alkoxy, alkoxyalkoxy, alkoxy halide, benzyloxy halide or alkanoyloxy.

A method of preparing the compounds of the present invention is as follows.

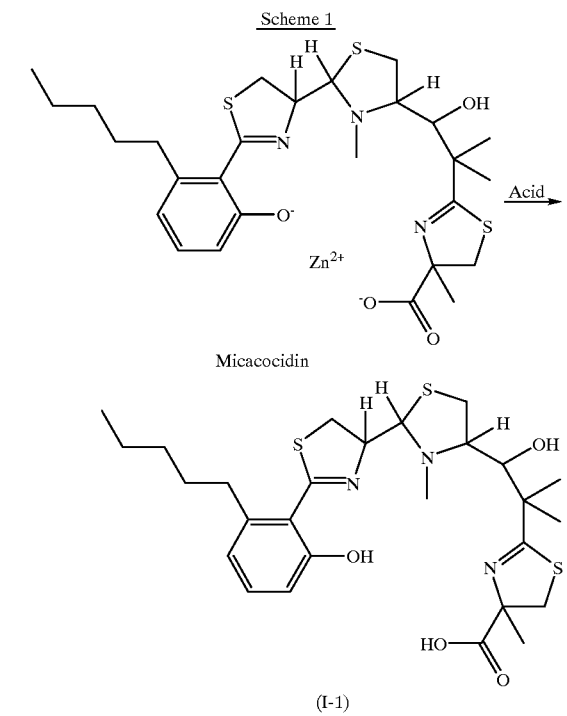

Scheme 1

Micacocidin (I-1)

The compound of the present invention (I-1) can be prepared by reacting micacocidin with an acid in an appropriate solvent.

The acid which can be used includes hydrochloric acid, sulfuric acid, potassium hydrogensulfate, and methane sulfonate. The acid is used in an amount of 2–50 equivalents, preferably 3–10 equivalents of micacocidin.

The solvent which can be used includes carbohydrate halides, such as dichloromethane, chloroform and the like;

esters, such as ethyl acetate and the like; ethers, such as diethylether, tetrahydrofuran and the like; alcohols, such as methanol, ethanol and the like; water; and mixtures thereof.

The reaction temperature is −20 to 50° C., preferably 0 to 35° C.

The reaction time is 1 minute to 1 hour, preferably 5 minutes to 0.5 hour.

The compound of the present invention (1-1) obtained can be purified by a conventional method, for example, column chromatography, recrystalization or the like.

Micacocidin used as a starting material in the reaction of Scheme 1 can be obtained as a culture product of a microorganism belonging to Genus Pseudomonas, for example, Pseudomonas sp. strain No. 57-250.

Cultivation of Pseudomonas sp. strain No. 57-250 can be performed in a liquid medium consisting of several compositions. A medium useful for producing micacocidin contains as a carbon source, for example, glucose, and as a nitrogen source, for example, yeast extract, soy bean powder, pharmamedia and the like. In addition, a metal salt such as zinc, copper, iron, or calcium carbonate is added for preparing the medium, if necessary. An antifoaming agent, such as polypropylene glycol can be added, if necessary. Cultivation is usually performed aerobically, preferably aeration culture with stirring. The cultivation temperature can suitably be changed in the range in which the microorganism can grow to produce micacocidin. However, especially preferable temperature is 23–28° C. The pH is preferably near 7, and the cultivation time is usually about 24 to 48 hours, and then, cultivation is discontinued at a proper time when the titer of micacocidin in the culture reaches to maximum level.

Recovery of micacocidin from the culture medium may be performed according to conventional methods for recovering fermentation products, for example, by extracting the product with non-hydrophilic organic solvents such as ethyl acetate, chloroform or the like, or by adsorbing the culture filtrate to synthetic partitioned porous resin (HP-20) or the like, which is then eluted with methanol or ethanol, and then, concentrating the eluate thus obtained in vacuo, followed by adding an organic solvent such as ethyl acetate to extract the product.

Micacocidin thus obtained can be used in the subsecuent steps without performing further purification, or after purified by the combination of well known methods usually used for purification of lipophilic substances, for example, thin layer chromatography and column chromatography using a carrier such as silica gel, or column chromatography using molecular sieve (LH-20 etc.), followed by crystallizing micacocidin by precipitating it from various mixed solvents, such as methanol-water, ethanol-water, methanol-ethyl acetate or the like.

Bacteriological property of Pseudomonas sp. strain No. 57-250 is shown below.

1. Morphology:
It is Gram-negative rod, and 0.5–0.6 μm×2.0–3.0 μm in size.

It has motility with one or more polar flagella.

2. Findings in Culture:
1) Culture in broth medium
A bit slow growth of bacteria, observed a slight yellowish white precipitate.

2) Stab culture in broth agar
Observed growth in thread form along the stab line with broad growth appeared on the surface of the medium.

No production of gas and pigment was observed.

3) Slant culture in broth agar

A bit slow growth of bacteria. Bacterial cells are yellowish white, dull glossy and wet. Flat swelling. Transparency: translucent in an early stage of culture, and then turned to opaque with the lapse of time. No production of gas and pigment was observed.

4) Cultivation on broth agar plate medium:
A bit slow growth of bacteria. Colony: translucent and yellowish-white small dot and thereafter growing into opaque and yellowish-white round form with flat or round swelling. No production of gas and soluble pigment was observed.

3. Physiological and Biochemical Properties
(1) Requirement of oxygen: Yes
(2) Optimal temperature for growth: 30° C. (well growing at 28° C. and 37° C., slow growing at 10° C., and not growing at 4° C. and 41° C.)
(3) Optimal pH for growth: pH 7 (grew at pH 5–8, but not grew at pH 4 and pH 9)
(4) Denitrification: negative
(5) Reduction of nitrate: negative
(6) Oxidase test: positive
(7) Urease test: positive
(8) Catalase test: positive (weakly)
(9) Liquefaction of gelatin: negative
(10) Starch degradation: negative
(11) Methyl red test: negative
(12) V-P test: negative
(13) Production of indole: negative
(14) Production of H2S: negative
(15) Availability of citric acid: positive (Christensen medium and Simons medium)
(16) Hydrolizing ability for Tween 80: positive (slow)
(17) Hydrolizing ability for escrine: negative
(18) Hydrolizing ability for arginine: negative
(19) Decarboxylation of lysin: negative
(20) Decarboxylation of ornithine: negative
(21) β-galactosidase: negative
(22) Coagulation of milk: negative
(23) Peptonization of milk: negative
(24) O-F test: oxidized (slow)
(25) Accumulation of PHB: negative
(26) Quinone type: Q8
(27) Fluorescent pigment: negative
(28) Acid-producing ability from sugar:
An acid is produced from D-glucose, D-galactose and D-xylose, and not produced from D-fructose, maltose, D-mannitol, lactose, sucrose, D-arabinose, D-sorbitol, D-mannose and D-trehalose.
(29) Assimilating ability of carbon sources
It can assimilate as a single carbon source D-glucose, D-galactose, D-xylose, inositol succinate and lactic acid to form the bacterial cells thereof.

On the other hand, it did not assimilate D-fructose, maltose, D-mannitol, lactose, sucrose, D-arabinose, D-sorbitol, D-mannose and D-trehalose, geraniol, L-valine, β-alanine, DL-arginine, betaine and methanol.

The growth of strain No. 57-250 in an inorganic salt medium containing a sole carbon source is very slow and weak.

In view of these results, the present bacteria are considered to belong to Pseudomonas. Therefore, their properties were further compared with those of Pseudomonas species described in Bergey's Manual of Systematic Bacteriology Vol.1, and it can be found that no species have properties consistent or analogous to those of the present bacteria. Thus, The bacteria was designated as Pseudomonas sp. No.57-250.

The strain was deposited under accession No. FERM P-14235 with National Institute of Bioscience and Human Technology, Higashi 1-1-3, Tsukuba, Ibaraki, JAPAN on Mar. 17, 1994 and then transferred to the International Deposition under Budapest Treaty on Jun. 22, 1995, and assigned to accession No. FERM BP-5143.

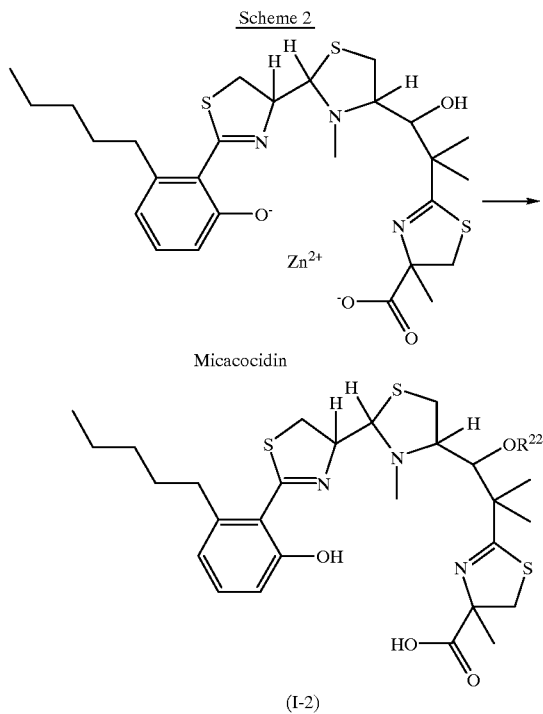

wherein $R^{22}$ represents optionally substituted alkyl, optionally substituted aralkyl, optionally substituted heteroaryl, optionally substituted heteroarylalkyl, $COR^{17}$ herein $R^{17}$ is as defined above, $COOR^{18}$ wherein $R^1$ is as defined above, or $CONR^{19}R^{20}$ wherein $R^{19}$ and $R^{20}$ are as defined above.

Out of the compounds of the present invention represented by the formula (I-2), the compound wherein $R^{22}$ is optionally substituted alkyl, optionally substituted aralkyl, optionally substituted heteroaryl or optionally substituted heteroarylalkyl can be prepared by alkylating or arylating micacocidin in an appropriate solvent in the presence or absence of a base, and then, if necessary, allowing to react with an acid. An alkylating agent or arylating agent includes, for example, diazoalkanes such as diazomethane, trimethylsilyldiazomethane or the like; alkyl halides such as iodomethane, bromomethane, benzyl bromide or the like; heteroaryl halides such as 2-chloropyridine, 4-chloropyridine or the like; heteroarylalkyl halides such as 2-(chloromethyl)benzoimidazol or the like; sulfates such as dimethyl sulfate, diethyl sulfate or the like; sulfonates such as ethyl methane sulfonate, phenethyl p-toluene sulfonate or the like; and chloromethylalkyl ethers such as chloromethylmethyl ether, chloromethylethyl ether or the like. They are used in an amount of 1–5 equivalents, preferably 1–3 equivalents of micacocidin.

A solvent which can be used in the reaction includes alcohols such as methanol, ethanol or the like; carbohydrate halides such as dichloromethane, chloroform, chlorobenzene or the like; esters such as ethyl acetate or the like; ethers such as diethyl ether, tetrahydrofuran, dioxane or the like; amides such as N,N-dimethylformamide, N,N-dimethylacetoamide or the like; sulfoxides such as dimethyl sulfoxide or the like; carbohydrates such as hexane, benzene, toluene or the like; ketones such as acetone, ethyl methyl ketone or the like; nitriles such as acetonitrile or the like; water; and a mixture thereof.

Bases to be employed include carbonates, for example, potassium carbonate, sodium carbonate and the like; alkali hydroxides, for example, potassium hydroxide, sodium hydroxide and the like; and amines, for example, triethyl amine, N,N-diisopropylethylamine and the like. They are used in an amount of 1–5 equivalents, preferably 1–3 equivalents of micacocidin.

The reaction temperature is −20 to 120° C., preferably 0 to 60° C., and the reaction time is 10 min. to 24 hrs., preferably 30 min. to 15 hrs.

The reaction with acids can be performed in the same manner as the reaction in Scheme 1 described above.

Out of the present compounds of the formula (I-2), the compound wherein $R^{22}$ is $COR^{17}$ can be prepared by acylating micacocidin in an appropriate solvent in the presence or absence of a base, and then, reacting the product with an acid if necessary.

Acylating agents include, for example, acid anhydrides such as acetic anhydride, benzoic anhydride and the like; acid halides, such as acethyl chloride, benzoyl chloride, phenylacethyl chloride and the like. They are used in an amount of 1–5 equivalents, preferably 1–3 equivalents of micacocidin.

Solvents to be used include carbohydrate halides such dichloromethane, chloroform, chlorobenzene and the like; esters such as ethyl acetate and the like; ethers such as diethyl ether, tetrahydrofurane, dioxane and the like; amides such as N,N-dimethylformamide, N,N-dimethylacetoamide and the like; sulfoxides such as dimethyl sulfoxide; carbohydrates such as hexane, benzene, toluene; ketones such as acetone, ethyl methyl ketone; nitriles such as acetonitrile; and the mixture thereof.

Bases to be used include carbonates such as potassium carbonate, sodium carbonate and the like; amines such as triethylamine, N,N-diisopropylethylamine and the like. The bases are used in an amount of 1–5 equivalents, preferably 1–3 equivalents of micacocidin.

The reaction temperature is −20 to 60° C., preferably 0 to 40° C., and the reaction time is 5 minutes to 24 hours, preferably 10 minutes to 8 hours.

The reaction with an acid can be performed in the same manner as the reaction in Scheme 1 previously stated. out of the present compounds of the formula (I-2), the compound wherein $R^{22}$ is $COOR^{18}$ can be prepared, in the presence or absence of a base, by carbonating micacocidin in an appropriate solvent, and then, reacting the product with an acid if necessary. The carbonating agents include, for example, halogenated carbonates such as ethyl chlorocarbonate, t-butyl bromocarbonate, phenyl chlorocarbonate, benzyl choloroarbonate and the like. They are used in an amount of 1–5 equivalents, preferably 1–3 equivalents of micacocidin.

Solvents to be used include carbohydrate halides such as dichloromethane, chloroform, chlorobenzene and the like; esters such as ethyl acetate and the like; ethers such as diethyl ether, tetrahydrofurane, dioxane and the like; amides such as N,N-dimethylformamide, N,N-dimethyacetoamide and the like; sulfoxides such as dimethyl sulfoxide; carbohydrates such as hexane, benzene, toluene; ketones such as acetone, ethyl methyl ketone; nitriles such as acetonitrile; and a mixture thereof.

Bases to be used include carbonates such as potassium carbonate, sodium carbonate; amines such as triethylamine, N,N-diisopropylethylamine. They are used in an amount of 1–5 equivalents, preferably 1–3 equivalents of micacocidin.

The reaction temperature is −20 to 60° C., preferably 0 to 40° C., and the reaction time is 5 minutes to 24 hours, preferably 10 minutes to 8 hours.

Reaction of the product with an acid can be performed in the same manner as the reaction in Scheme 1 stated above.

Out of the compounds of the formula (I-2) of the present invention, the compound wherein $R^{22}$ is $COR^{19}R^{20}$ can be prepared, in the presence of or the absence of a base, by carbamoyling micacocidin in an appropriate solvent, and then, reacting the product with an acid, if necessary.

The carbamoyling agents include, for example, isocyanates such as methyl isocyanate, phenyl isocyanate, benzyl isocyanate and the like; carbamyl halides such as dimethylcarbamyl chloride and the like. They are used in an amount of 1–5 equivalents, preferably 1–3 equivalents of micacocidin.

Solvents to be used include halogenated carbohydrates such as dichloromethane, chloroform, chlorobenzene and the like; esters such as ethyl acetate and the like; ethers such as diethyl ether, tetrahydrofurane, dioxane and the like; amides such as N,N-dimethylformamide, N,N-dimethylacetoamide and the like; sulfoxides such as dimethyl sulfoxide; carbohydrates such as hexane, benzene, toluene and the like; ketones such as acetone, ethyl methyl ketone; nitrites such as acetonitrile; and a mixture thereof.

Bases to be used include carbonates such as potassium carbonate, sodium carbonate and the like; amines such as triethylamine, N,N-diisopropylethylamine and the like. They are used in an amount of 1–5 equivalents, preferably 1–3 equivalents of micacocidin.

The reaction temperature is –20 to 60° C., preferably 0 to 40° C., and the reaction time is 5 minutes to 24 hours, preferably 10 minutes to 8 hours.

The reaction of the product with an acid can be performed in the same manner as the reaction described in Scheme 1.

The compound (I-2) of the present invention thus obtained can be purified by conventional methods such as column chromatography, recrystallization and the like, if necessary.

above, $COOR^{14}$ wherein $R^{14}$ is as defined above, or $CONR^{15}R^{16}$ wherein $R^{15}$ and $R^{16}$ are as defined above.

Out of the compounds of the formula (I-3) of the present invention, the compound wherein $R^{21}$ is optionally substituted alkyl, optionally substituted aralkyl, optionally substituted heteroaryl or optionally substituted heteroarylalkyl, can be prepared, in the presence or absence of a base, by alkylating or arylating the compound of the present invention in an appropriate solvent, followed by hydrolyzing the product with a base in an appropriate solvent, if necessary.

The alkylation or arylation can be performed in the same manner as the reaction described in Schema 2. Bases to be used in the hydrolysis include carbonates such as potassium carbonate, sodium carbonate and the like; alkali hydroxides such as sodium hydroxide, potassium hydroxide and the like. They are used in an amount of 1–3 equivalents, preferably 1–2 equivalents of the compound (I-1).

Solvents to be used include alcohols such as methanol, ethanol and the like; ethers such as diethyl ether, tetrahydrofuran, dioxane and the like; carbohydrates such as hexane, benzene, toluene and the like; ketones such as acetone, ethyl methyl ketone and the like; water; and a mixture thereof.

The reaction temperature is –20 to 120° C., preferably 0 to 40° C., and the reaction time is 10 minutes to 24 hours, preferably 30 minutes to 15 hours.

Out of the compounds of the formula (I-3) of the present invention, the compound wherein $R^{21}$ is $COR^{13}$ can be prepared, in the presence or absence of a base, by acylating the compound (I-1) of the present invention in an appropriate solvent.

Acylation can be performed in the same manner as the reaction in Scheme 2.

Out of the present compounds of the formula (I-3), the compound wherein $R^{21}$ is $COOR^{14}$ can be prepared, in the presence or absence of a base, by carbamoyling the compound (I-1) of the present invention in an appropriate solvent.

Carbonation can be performed in the same manner as the reaction in Scheme 2.

Out of the present compounds of the formula (I-3), the compound wherein $R^{21}$ is $CONR^{15}R^{16}$ can be prepared, in the presence or absence of a base, by carbamoyling the compound (I-1) of the present invention in an appropriate solvent.

Carbamoylation can be performed in the same manner as the reaction in Scheme 2.

The compound (I-3) of the invention thus obtained can be optionally purified by a conventional method, for example, column chromatograpy, recrystalization and the like.

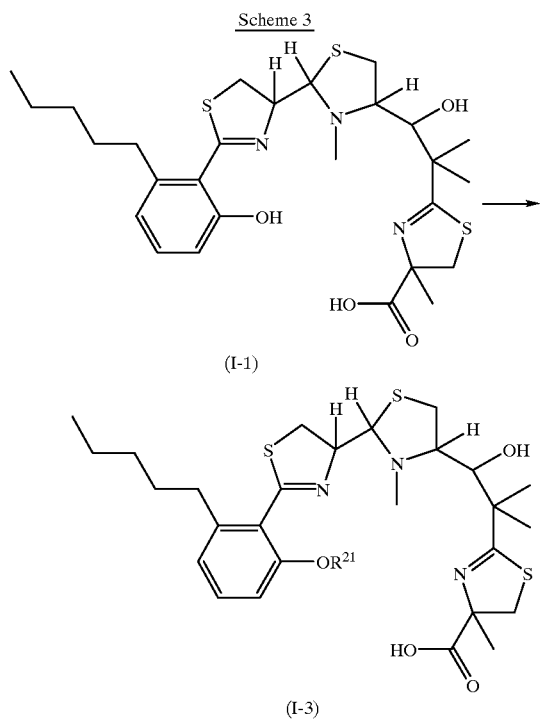

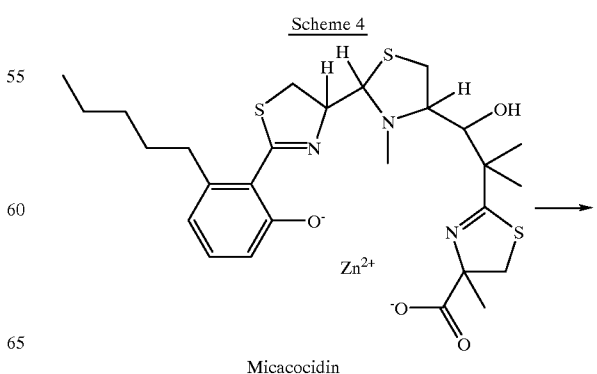

wherein $R^{21}$ is optionally substituted alkyl, optionally substituted aralkyl, optionally substituted heteroaryl, optionally substituted heteroarylalkyl, $COR^{13}$ wherein $R^{13}$ is as defined

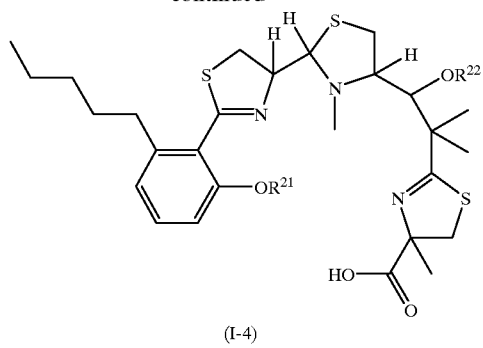

(I-4)

wherein $R^{21}$ and $R^{22}$ are the same or different and as defined above.

Out of the compounds of the formula (I-4) of the present invention, the compound wherein $R^{21}$ and $R^{22}$ are the same and represent optionally substituted alkyl, optionally substituted aralkyl, optionally substituted heteroaryl or optionally substituted heteroarylalkyl, can be prepared, in the presence or absence of a base, by alkylating or arylating micacocidine in an appropriate solvent.

Alkylation or arylation can be performed in the same manner as the reaction described in Scheme 2. Out of the present compounds of the formula (I-4), the compound wherein $R^{21}$ is $COR^{13}$ and $R^{22}$ is $COR^{17}$, can be prepared, in the presence or absence of a base by acylating micacocidin in an appropriate solvent.

Acylation can be performed in the same manner as the reaction in Scheme 2 stated above.

Out of the present compounds of the formula (I-4), the compound wherein $R^{21}$ is $COOR^{14}$ and $R^{22}$ is $COOR^{18}$ can be prepared, in the presence or absence of a base, by carbonating micacocidine in an appropriate solvent.

Carbonation can be performed in the same manner as the reaction in Scheme 2 stated above. Out of the present compounds of the formula (I-4), the compound wherein $R^{21}$ is $CONR^{15}R^{16}$ and $R^{22}$ is $CONR^{19}R^{20}$, can be prepared, in the presence or absence of a base, by carbamoyling micacocidin in an appropriate solvent. Carbamoylation can be performed in the same manner as the reaction in Scheme 2 stated above.

Out of the compounds of the formula (I-4) of the present invention, the compound wherein $R^{21}$ and $R^{22}$ are different from each other, can be prepared by subjecting the compound of the formula (I-3) of the present invention which was obtained according to Scheme 3 stated above to the same reaction as that in Scheme 2 stated above to introduce the substituent $R^{22}$ which differs from $R^{21}$.

The compound (I-4) of the invention thus obtained can be optionally purified by conventional methods such as column chromatography and recrystalization, or it is obtained by subjecting the compound (I-2) obtained by the reaction in Scheme 2 to the same reaction as that in Scheme 3 and then subjecting the product to hydrolysis or catalytic reduction, if necessary.

Scheme 5

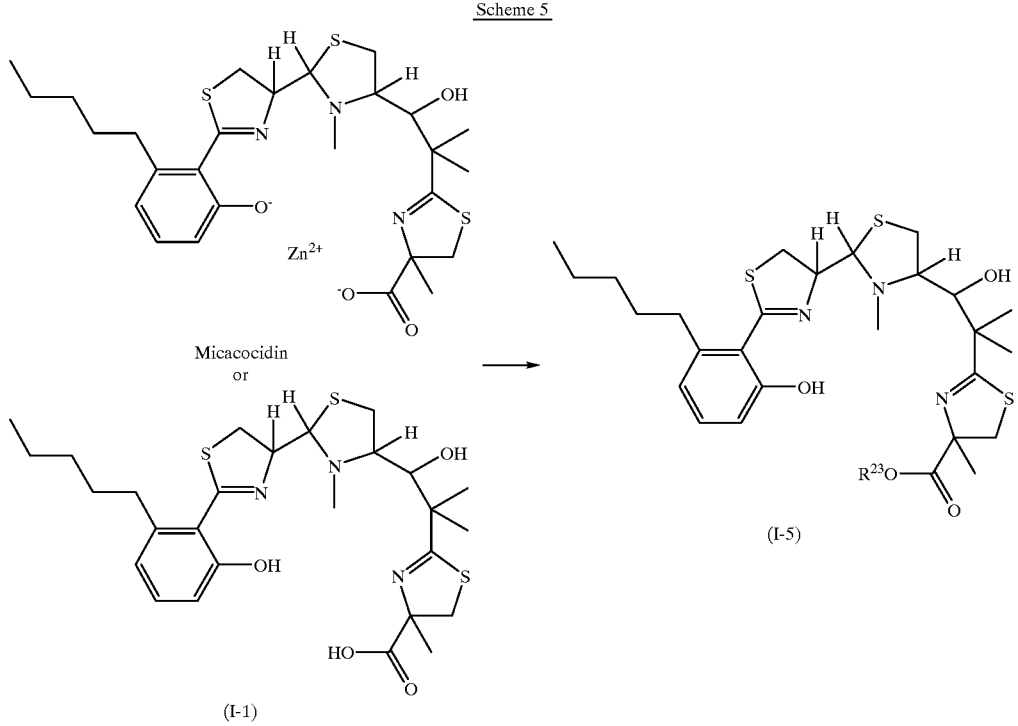

wherein $R^{23}$ presents optionally substituted alkyl, optionally substituted aralkyl, optionally substituted heteroaryl or optionally substituted heteroarylalkyl.

The compound of the the formula (I-5) of the invention can be prepared by alkylating or arylating micacocidine or the compound (I-1) of the present invention in an appropriate solvent in the presence or absence of a base.

Alkylation or Arylation can be performed in the same manner as the reaction of Scheme 2 stated above, provided that the alkylating or arylating agent and a base are used in an amount of 1–3 equivalents, preferably 1–1.5 equivalents for micacocidin or the compound (I-1). The compound (I-5) can also be prepared by allowing the compound (I-2) to react, in the presence of a dehydrating agent, for example, dicyclohexylcarbondiimide, with the corresponding alcohol ($R^{23}OH$), or converting the compound (I-2) to the reactive derivative such as acid chloride or activated ester, and then reacting the product with $R^{23}OH$.

The compound (I-5) of the present invention thus obtained can optionally be purified by conventional manner, for example, by column chromatography and recrystalization.

hydroxylamine, N-methylhydroxylamine, methoxylamine; and hydrochloride thereof. They are used in an amount of 1–5 equivalents, preferably 1–2 equivalents of micacocidin or the compound (I-1).

Solvents to be used include carbohydrate halides such as dichloromethane, chloroform, chlorobenzene and the like; ethers such as diethyl ether, tetrahydrofurane, dioxane and the like; amides such as N,N-dimethylformamide, N,N-dimethylacetoamide; sulfoxides such as dimethyl sulfoxide; carbohydrates such as hexane, benzene, toluene; ketones such as acetone, ethylmethyl ketone; nitrites; and a mixture thereof.

Bases to be used include amines such as triethylamine, N,N-diisopropylethylamine. They are used in an amount of 1–5 equivalents, preferably 1–3 equivalents of micacocidin or the compound (I-1).

Condensing agents to be used include carbodiimides such as 1,3-dicyclohexylcarbodiimide (DCC), diethyl cyanophosphate (DEPC), diphenyl phosphorylazide (DPPA),

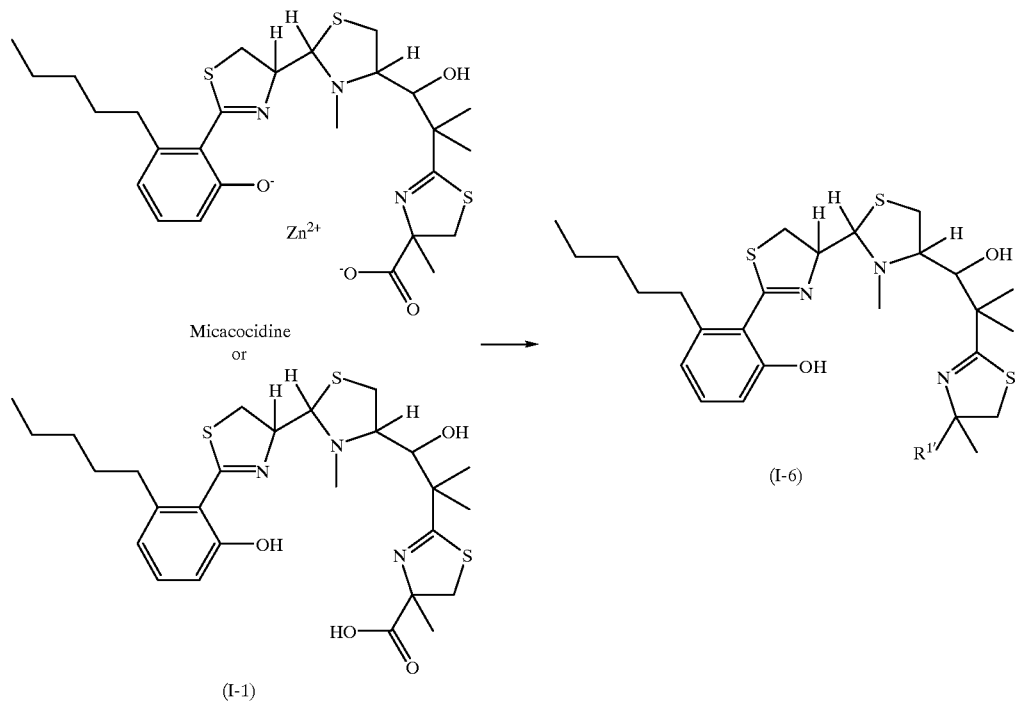

wherein $R^{1'}$ represents $CONR^5R^6$ wherein $R^5$ and $R^6$ are as defined above, or $CO-R^7-OR$ wherein $R^7$ and R are as defined above.

The compound of the the formula (I-6) can be prepared, in the presence or absence of a base, through amidation of micacocidin or the compound (I-1) of the present invention by condensing them with an amine using an appropriate condensing agent in an appropriate solvent.

The amines include for example α-amino acid ester such as L-alanine methyl ester, L-seline methyl ester, L-cystine methyl ester; alkyl amines such as methylamine, ethanolamine, dimethylamine; hydroxylamines such as benzotriasol-1-yloxytris(dimethylamino)phosphonium-hexafluorophosphate (Bop reagent), bis (2-oxo-3-oxazolidinyl) phosphinic chloride (BOP-Cl). They are used in an amount of 1–5 equivalents, preferably 1–2 equivalents of micacocidin or the compound (I-1).

The reaction temperature is −20 to 80° C., preferably 0 to 40° C., and the reaction time is 5 minutes to 24 hours, preferably 30 minutes to 15 hours.

The compound (I-6) thus obtained can optionally be purified by conventional methods such as column chromatography, thin layer chromatography, and recrystalization.

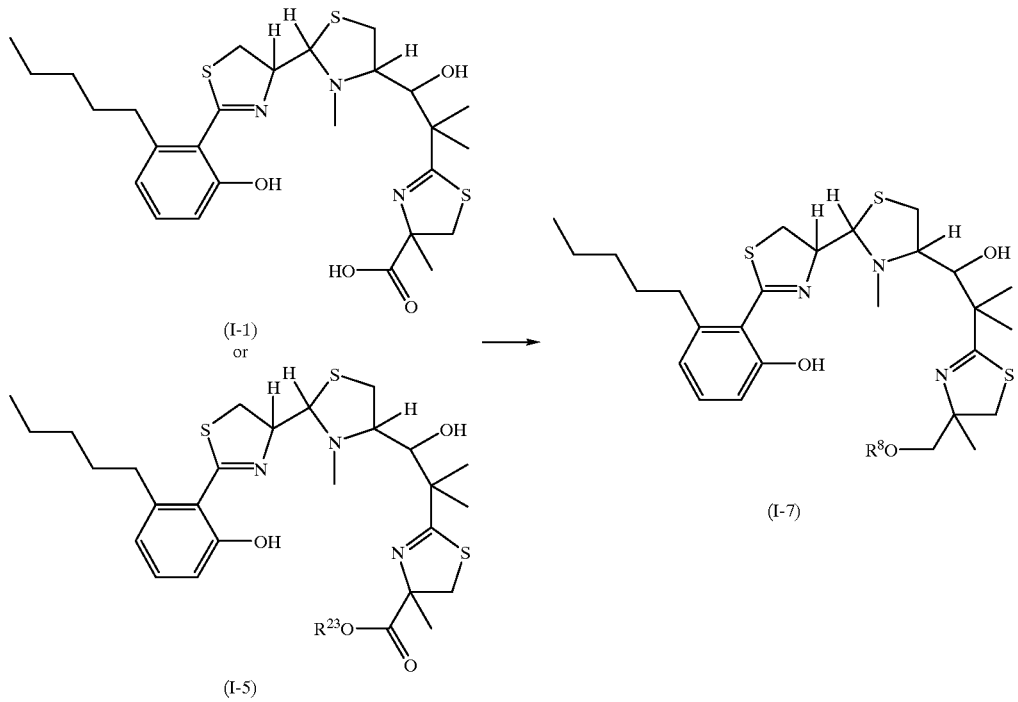

Scheme 7 wherein $R^8$ and $R^{23}$ are as defined above.

The compound of the formula (I-7) of the present invention can be prepared by reducing the compound (I-1) or (I-5) in an appropriate solvent.

The reducing agents include boron compounds, such as diborane, and lithium boron hydride; aluminum compounds such as lithium aluminum hydride, and diisobutyl aluminum hydride. The reducing agents are used in an amount of 1–5 equivalents, preferably 1–3 equivalents of compound (I-1) or the compound (I-5).

Solvents to be used include ethers such as diethyl ether, tetrahydrofuran, dioxane; carbohydrates such as hexane, benzene, and toluene.

The reaction temperature is −78 to 60° C., preferably −78 to 40° C., and the reaction time is 10 minutes to 24 hours, preferably 30 minutes to 15 hours.

The compound (I-7) thus obtained can optionally be purified by conventional methods such as column chromatography, thin layer chromatography, and recrystallization.

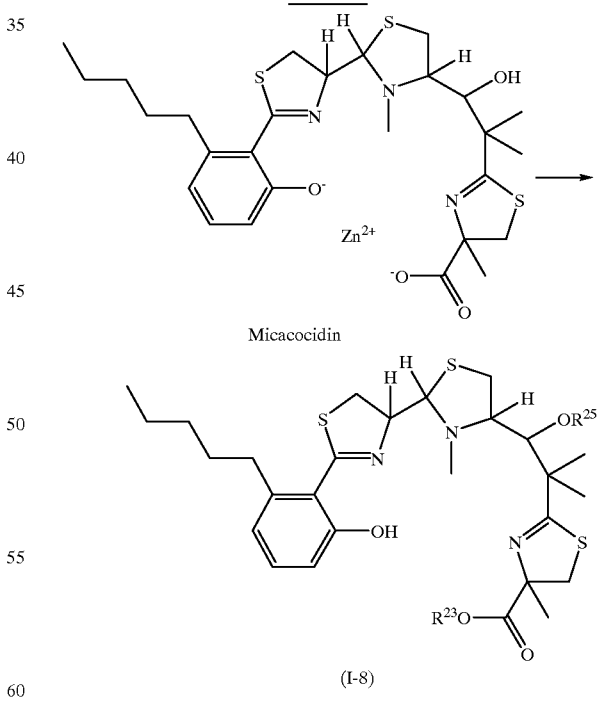

Scheme 8

Micacocidin wherein $R^{23}$ and $R^{25}$ are the same or different and represent optionally substituted alkyl, optionally substituted aralkyl, optionally substituted heteroaryl or optionally substituted heteroarylalkyl.

Out of the compounds of the formula (I-8), the compound wherein $R^{23}$ and $R^{25}$ are the same, can be prepared, in the presence or absence of a base, by alkylating or arylating micacocidin in an appropriate solvent. Alkylation or arylation can be accomplished in the same manner as the reaction of Scheme 2 mentioned above. Out of the compounds of the formula (I-8), the compound wherein $R^{23}$ and $R^{25}$ differ from each other, can be prepared, for example, by subjecting the compound of the formula (I-2) to the same reaction as that in Scheme 3 mentioned above to introduce $R^{23}$ which differs from $R^{22}$ of the formula (I-2).

The compound (I-8) thus obtained can optionally be purified by in conventional manner, for example, by column chromatography, thin layer chromatography, or recrystalization.

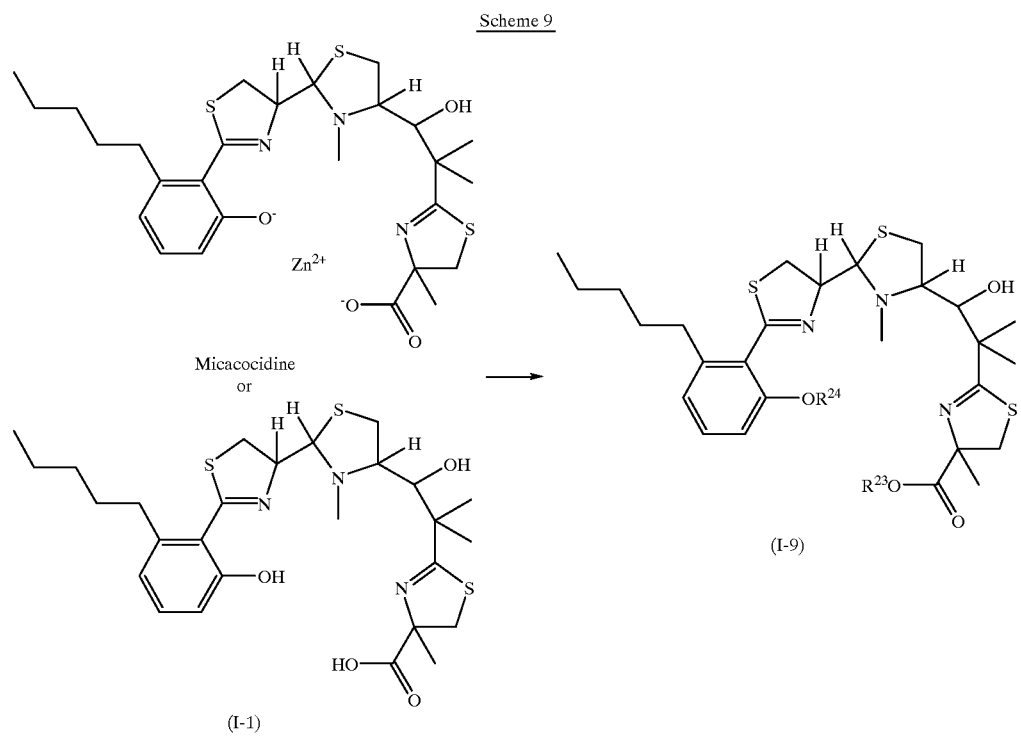

wherein $R^{23}$ and $R^{24}$ are the same or different and represent optionally substituted alkyl, optionally substituted aralkyl, optionally substituted heteroaryl or optionally substituted heteroarylalkyl.

Out of the compounds of the formula (I-9), the compound wherein R and R24 are the same, can be prepared, in the presence or absence of a base, by alkylating or arylating micacocidine or the compound (I-1) in an appropriate solvent.

Alkylation or arylation can be accomplished in the same manner as the reaction of Scheme 2 stated above. Out of the compounds of the formula (I-9), the compound wherein $R^{23}$ and $R^{24}$ are different from each other, can be prepared, for example, by subjecting the compound of the formula (I-5) to the same reaction as that in Scheme 3 stated above to introduce $R^{24}$ which differs from $R^{23}$ of the formula (I-5).

The compound (I-9) thus obtained can optionally be purified in conventional manner, for example, by column chromatography, thin layer chromatography, are recrystalization.

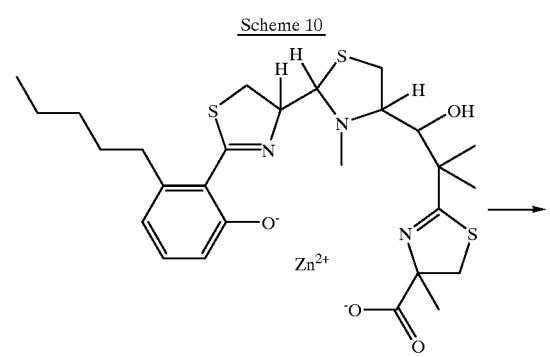

-continued

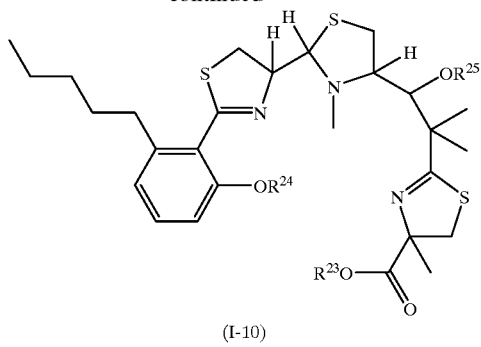

(I-10)

wherein $R^{23}$, $R^{24}$ and $R^{25}$ are as defined above.

Out of the compounds of the formula (I-10), the compound wherein $R^{23}$, $R^{24}$ and $R^{25}$ are identical, can be prepared, in the presence or absence of a base, by alkylating or arylating micacocidine in an appropriate solvent.

Alkylation or arylation can be accomplished in the same manner as the reaction of Scheme 2 stated above.

Out of the compounds of the formula (I-10), the compound wherein any one of $R^{23}$ and $R^{24}$ and $R^{25}$ is different from others, can be prepared, for example, by subjecting the compound of the formula (I-4), (I-8) or (I-9) to the same reaction as that in Scheme 5, 3 or 2 stated above, respectively, to introduce a different substituent.

The compound (I-10) thus obtained can optionally be purified by conventional methods such as column chromatography, thin layer chromatography, and recrystalization.

Scheme 11

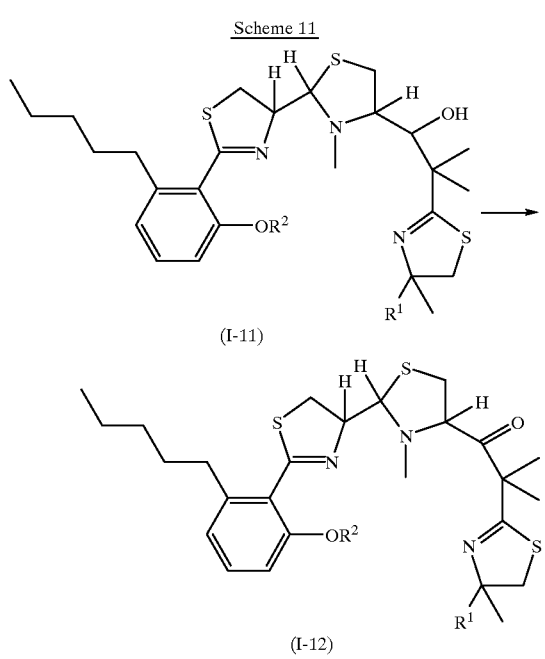

wherein $R^1$ and $R^2$ are as defined above.

The compound of the formula (I-12) can be prepared by oxidizing the compound of the formula (I-11).

The oxidizing agents include dimethyl sulfoxide (DMSO) used in the presence of an appropriate electrophilic reagent in the presence or absence of a base. They are used in an amount of 1–5 equivalents, preferably 1–3 equivalents of the compound of the formula (I-11).

Bases to be used with DMSO as an oxidizing agent include amines such as triethylamine, N,N-diisopropylethylamine. They are used in an amount of 1–5 equivalents, preferably 1–3 equivalents of the compound of the formula (I-11).

The electrophilic reagents to be used with DMSO as an oxidizing agent include, for example, carbodiimides such as 1,3-dicyclohexylcarbodiimide (DCC); acid anhydrides such as acetic anhydride; acid chlorides such as oxalyl chloride; pyridine-sulfur trichloride complex. They are used in an amount of 1–5 equivalents, preferably 1–3 equivalents of the compound of the formula (I-11).

The reaction temperature is −78 to 60° C., preferably −78 to 40° C., and the reaction time is 10 minutes to 24 hours, preferably 30 minutes to 15 hours.

The compound of the present invention (I-12) thus obtained can optionally be purified by a conventional method, for example, column chromatography, thin layer chromatography, recrystalization, etc. The compound of the present invention represented by the formula (I-11) which is used as a starting material in this reaction can be prepared by combining the reactions mentioned above.

The compound of the present invention may form a salt through its carboxylic acid moiety. Such salts are alkali metal salts, such as sodium salt, potassium salt and lithium salt; ammonium salt; and organic salts, such as methyl ammonium salt, dimethyl ammonium salt, triethyl ammonium salt, tetrabuthyl ammonium salt and the like.

The compound of the present invention represented by the formula (I) can be reacted with an aqueous solution of a bivalent or trivalent metal salt, such as chloride, sulfate or nitrate, to obtain a metal complex.

Bivalent or trivalent metals include $Zn^{2+}$, $Cu^{2+}$, $Fe^{2+}$, $Fe^{3+}$, $Co^{2+}$, $Ni^{2+}$, $Mn^{2+}$, $Mn^{3+}$, $Co^{2+}$, $Mg^{2+}$, $Ca^{2+}$, $Sr^{2+}$, $Ba^{2+}$, $V^{2+}$, $V^{3+}$, $Cr^{2+}$, $Al^{3+}$, $Sn^{2+}$, $Pb^{2+}$, $Ag^{2+}$ or the like.

The present invention further provides a pharmaceutical composition or a veterinary medicine containing the compound represented by the formula (I) of the present invention in combination with one or more pharmaceutical acceptable carriers.

The compound represented by the formula (I) of the present invention has, among others, anti-mycoplasma activity, antibacterial activity, antifungal activity and immunosuppressive activity, and therefore, can be used as an anti-mycoplasma agent, antibacterial agent, antifungal agent and immunosuppressor.

When used as a medicament, the compound of the invention can be orally or parenterally administered. For oral administration, the compound of the present invention can be formulated into conventional formulations, such as a solid formulation such as tablets, powders, granules and capsules; aqueous solutions; oily suspensions; or liquid preparations such as syrups or elixirs. For parenteral administration, it can be formulated into aqueous or oily suspensions, or suppositories. Each of them can be produced using carriers such as conventional excipients, binders, aqueous and oily solvents, emulsions and suspensions, if necessary, and optionally contains other additives such as preservatives or stabilizing agents.

The compound of the present invention is usually administered at a dose of 100–2000 mg per day, preferebly 500–100 mg per day, which may be divided into 1 to 5 portions, although the dose will vary depending on the administration route, ages, weights and the condition of patients, and the type of diseases.

When used as a veterinary medicine, it can be orally or parenterally administered to domestic fowls and animals such as chickens, swine and cattle. Generally, for oral administration, it is administered in combination with a commonly used carrier (such as defatted rice bran, defatted soy bean meal, wheat bran, kaolin, talc, calcium carbonate, lactic acid and water). However, it is preferable that such combination or the compound of the present invention is administered after combined with feed for animals or water. The feed for animals may be the ones which are commonly used as feed for animals, such as corn, wheat bran, rice, wheat, cotton seed meal, milo, soy bean meal, fish meal, defatted rice bran, oils and fats, alfalfa, calcium carbonate, calcium phosphate, sodium chloride, choline chloride, vitamins such as vitamin A, vitamin D, vitamin E, vitamin B1, vitamin B2, vitamin B6, vitamin B12, calcium pantothenate, nicotinic acid amide and folic acid, and inorganic salts such as magnesium sulfate, ferric sulfate, cupric sulfate, zinc sulfate, potassium iodide and cobalt sulfate. Part or all of them may be combined to use.

The contents of the compound of the present invention in feed are in the range of 100–2000 ppm, and preferably 500–1000 ppm.

For parenteral administration, it can be used in the same manner as that of the aforementioned medicament.

The compound of the present invention is generally administered at a dose of 50–2000 mg, preferably 100–500 mg for oral administration, and 50–100 mg, preferably 10–50 mg for parenteral administration, per kg of body weights of animal per day. The compound is administered for several consecutive days.

EXAMPLES

The present invention will be described in detail by means of, but not limited to, the following Reference Examples and Working Examples.

REFERENCES

Preparation of Mycacocidin by Culturing Pseudomonas sp. No. 57-250
1) Seed Culture
Bennet medium (1% glucose, 0.2% yeast extract, 0.1% meat extract and 0.2% casamino acid, pH 7) was autocraved at 121° C. for 20 min. and Pseudomonas sp. No.57-250 was inoculated and cultured at 28° C. using a rotary shaker at 140 rpm for 18 hours.
2) Main Culture
Eighty L of fermentation medium (1% glucose, 2% dextrin, 1% yeast extract, 1% Pharmamedia, 0.0002% cupric sulfate hexahydrate, 0.01% zinc sulfate heptahydrate, pH 6.5) was added to jars (2×50 L, 2×30 L) followed by adding anti-foaming agent (Polypropylene glycol 2000) at a final concentration of 0.01%. After sterilizing at 121° C. for 20 min. and cooling, the seed culture was inoculated at a final concentration of 1%. Then, they were cultured under the following conditions: at 28° C., agitating at 290–600 rpm, aerating at 25 L/min. for 50-L jar and 15 L/min. for 25-L jar, cultured for 42 hours.
3) Extraction and Isolation
(1) To 8.5 L of culture (pH 8.3), the equal amount of ethyl acetate was added and then liquid-liquid preparative extraction was performed twice. 760 mg of the culture was fractioned by column chromatography (140 g of silica gel, 70–230 mesh, Merck No.7734). Micacocidin was eluted with dichloromethane/methanol (95:5, v/v) solvent to give 11 mg of crude elute, and then, the eluate was partitioned to purify using thin layer chromatography (silica gel plate, 20×20 cm, 0.5 mm, Merck No.5744). Thus, after said eluate was developed 15-cm with chloroform/methanol (9:1, v/v) solvent, a bright blue band (irradiation with a UV lamp at 365 nm) around Rf value 0.5 was collected and extracted with a mixture of chloroform/methanol (8:2, v/v) to elute micacocidin. Further purification was conducted with a Sephadex LH-20 column (ID 15 mm×870 mm). Thus, the sample was dissolved in a small amount of methanol, followed by isolation with methanol. A fraction (6.6 mg) containing micacocidin was recrystallized from methanol/ethyl acetate to give 3.6 mg of colourless and rhombic board-shaped crystals. m.p.: 226–228° C. (Decomposition).

(2) About 70 L of the culture was centrifuged and separated into 66 L of the supernatant and the bacterial cells. 3.3 kg of HP-20 was added to the supernatant and agitated at room temperature for 1 hour. HP-20 was filtrated by a mesh filter, washed with water and then filled in a column. After washing with 40 L of deionized water, the elution with methanol gives 12 L of the active fraction. The fraction was concentrated in vacuo and then eluted with ethyl acetate. On the other hand, the bacterial cells were extracted with methanol, which was filtered, concentrated in vacuo and the residue was extracted with ethyl acetate. The ethyl acetate extracts obtained above from the supernatant and the bacterial cells were combined and concentrated to dryness, resulting in 11.3 g of a crude extract.

The crude extract was dissolved in chloroform, charged in a silica gel column (350 g of silica gel, column: 50×350 mm) and then developed with chloroform-methanol. After washing with 500 mL of chloroform and 1.6 L of chloroform-methanol (98:2), the column was eluted with 1.3 L of chloroform-methanol (9:1) to give 5.7 g of a crude fraction containing compound B. Repeated recrystallization of the crude fraction from ethyl acetate-methanol provided 1.73 g of compound B (micacocidin) as crystals.

Example 1

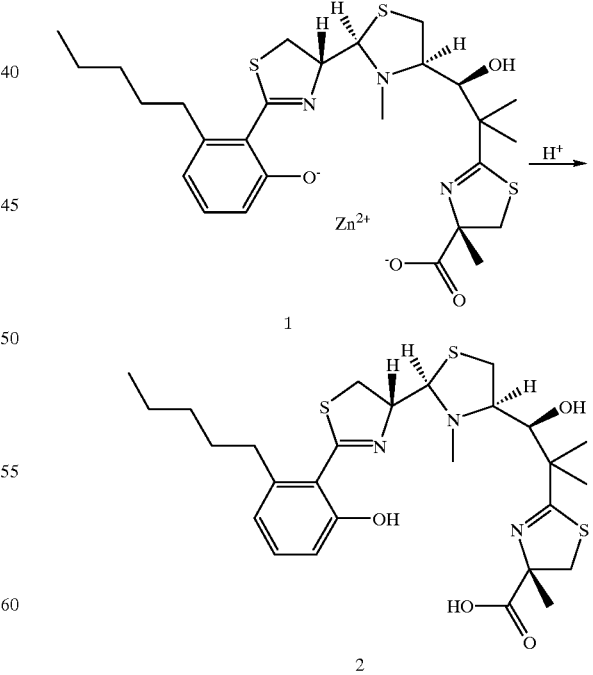

Two mg of micacocidin (hereinafter referred to as Compound 1) was dissolved in 2 mL of dichloromethane, followed by shaking with 4 mL of 1N hydrochloric acid (or 5% potassium hydrogen sulfate) with stirring. The dichloromethane layer was washed and dried in vacuo to give 1.8 mg of compound 2.

Molecular formula: $C_{27}H_{39}N_3O_4S_3$; SIMS m/z=566[M+H]$^+$; $^1$H-NMR(CDCl$_3$):0.90 ppm(3H, t, J=7.1 Hz), 1.31 ppm(3H, s), 1.32 ppm(3H, s), 1.32–1.38 ppm(4H, m), 1.59 ppm(3H, s), 1.59–1.63 ppm(2H, m), 2.63 ppm(3H, s), 2.86–3.02 ppm(3H, m), 3.17 ppm (1H, dd, J=11.2 Hz, 7.8 Hz), 3.18 ppm(1H, d, J=11.5 Hz), 3.26 ppm (1H dd, J=11.2 Hz, 7.1 Hz), 3.34 ppm(1H, m), 3.47 ppm(1H, dd, J=11.2 Hz, 8.8 Hz), 3.61 ppm(1H, d, J=6.8 Hz), 3.65 ppm(1H, d, J=11.5 Hz), 4.21 ppm(1H, d, J=8.7 Hz), 4.76 ppm(1H, ddd, J=8.8 Hz, 8.7 Hz, 7.8 Hz), 6.71 ppm(1H, dd, J=7.8 Hz, 1.2 Hz), 6.85 ppm(1H, dd, J=8.3 Hz, 1.2 Hz), 7.21 ppm(1H, dd, J=8.3 Hz, 7.8 Hz). $^{13}$C-NMR(CDCl$_1$):14.05 ppm(q), 22.50 ppm(t), 23.89 ppm(q), 24.15 ppm(q), 24.20 ppm(q), 31.89 ppm(t), 32.17 ppm(t), 35.03 ppm(t), 35.40 ppm (t), 36.73 ppm(t), 41.12 ppm(t), 45.61 ppm(s), 46.12 ppm(q), 72.72 ppm(d), 78.04 ppm(d), 78.08 ppm(d), 79.35 ppm(d), 83.87 ppm (s), 115.43 ppm(d), 116.29 ppm(s), 121.46 ppm(d), 132.25 ppm (d), 143.80 ppm(s), 159.57 ppm(s), 172.11 ppm(s), 175.08 ppm(s), 181.87 ppm(s).

Molecular formula: $C_{28}H_{41}N_3O_4S_3$; FAB MS: m/z=580 [M+H]$^+$; $^1$H-NMR(CDCl$_3$): 0.89 ppm(3H, t, J=7.1 Hz), 1.27 ppm(3H, s), 1.30–1.34 ppm(4H, m), 1.36 ppm(3H, s), 1.39 ppm(3H, s), 1.57–1.65 ppm(2H, m), 2.54 ppm(3H, s), 2.59–2.63 ppm(2H, m), 2.99 ppm(1H, dd, J=11.5 Hz, 5.1 Hz), 3.03 ppm(1H, d, J=11.7 Hz), 3.24 ppm(1H, dd, J=11.5 Hz, 7.3 Hz), 3.27 ppm(1H, dd, J=11.2 Hz, 9.0 Hz), 3.32 ppm(1H, dt, J=7.3 Hz, 5.1 Hz), 3.50 ppm(1H, d, J=5.1 Hz), 3.57 ppm(1H, dd, J=11.2 Hz, 8.5 Hz), 3.73 ppm(1H, d, J=11.7 Hz), 3.81 ppm(3H, s), 4.30 ppm(1H, d, J=9.3 Hz), 4.91 ppm(1H, ddd, J=9.3 Hz, 9.0 Hz, 8.5 Hz), 6.73 ppm(1H, d, J=7.8 Hz), 6.82 ppm(1H, d, J=7.3 Hz), 7.25 ppm(1H, dd, J=7.8 Hz, 7.3 Hz). $^{13}$C-NMR(CDCl$_3$):14.03 ppm(q), 22.53 ppm(t), 23.92 ppm(q), 24.57 ppm (q), 26.21 ppm(q), 30.79 ppm(t), 31.81 ppm(t), 32.72 ppm(t), 37.04 ppm (t), 37.21 ppm(t), 40.79 ppm(t), 45.24 ppm(s), 45.75 ppm(q), 55.95 ppm (d), 71.97 ppm(d), 78.93 ppm(d), 80.55 ppm(d), 81.25 ppm(d), 84.26 ppm (s), 108.45 ppm(d), 121.38 ppm(d), 122.54 ppm(s), 130.16 ppm(d), 142.55 ppm(s), 156.94 ppm (s), 168.16 ppm(s), 174.57 ppm(s), 181.33 ppm (s).

Example 2

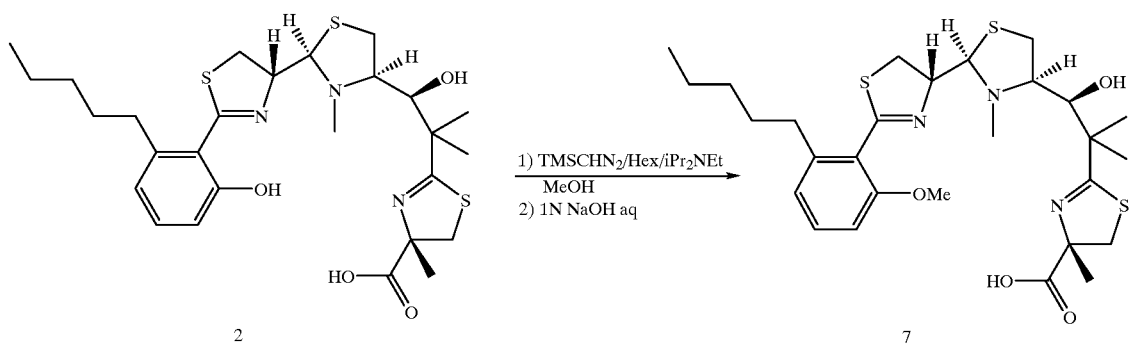

Eighty eight mg (0.15 mM) of compound 2 was dissolved in 1.0 mL of methanol. To the solution were added 29.7 mg (0.23 mM) of N-diisopropylethylamine at room temperature, and then, 0.12 mL (0.24 mM) of a 2M trimethylsilyldiazomethane solution with stirring at room temperature, followed by stirring over night. After completion of the reaction, 3 mL of methanol was added. Subsequently, 2 mL of 1N sodium hydroxide were added under ice-cooling, followed by stirring for one hour at room temperature. The reaction was adjusted to pH 6 with 2N hydrochloric acid under ice-cooling, extracted 3 times with dichloromethane, washed 2 times with water, and then, dried with anhydrous sodium sulfate. Then, the solvent was evaporated to obtain 65 mg of crude product. Isolating and purifying the product using PHLC gives the purposed compound 7.

Example 3

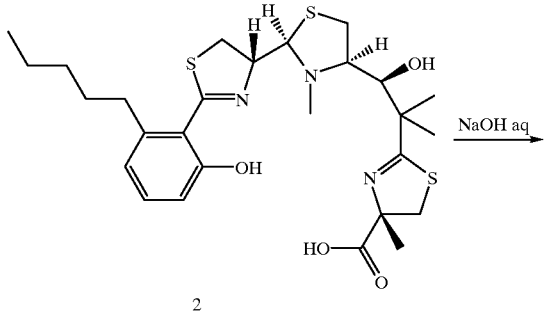

-continued

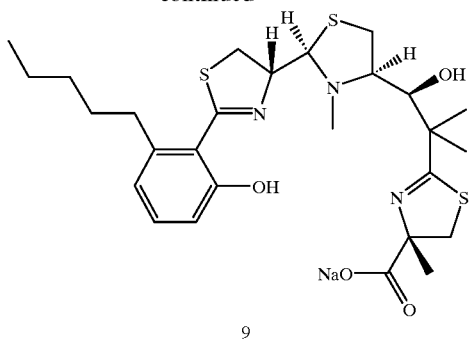

9

8.9 mg (94.9% contained) of compound 2 was dissolved in 1 mL of methanol, to which 15.58 μL of 1N sodium hydroxide was added and stirred. After few minutes, the mixture was evaporated to dryness in vacuo, and the residue was dissolved in 0.5 ml of water and lyophilized to give 9 mg of compound 9.

Molecular formula: $C_{27}H_{38}N_3O_4S_3Na$

Example 4

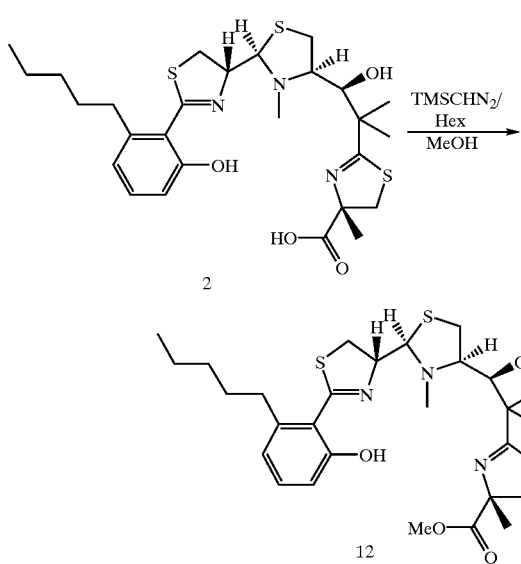

150 mg (0.265 mM) of compound 2 was dissolved in 2 mL of methanol, to which 0.74 ml (0.37 mM) of a 2 M trimethylsilyldiazomethane/hexane solution was added at room temperature with stirring. The mixture was kept standing for 50 minutes at room temperature and concentrated, and then, purified by PTLC to give 88 mg of oily compound 12. A sample for identification of the structure and assay was further purified by HPLC.

Molecular formula: $C_{28}H_{41}N_3O_4S_3$; SIMS: m/z=580[M+H]$^+$; $^1$H-NMR(CDCl$_3$): 0.88 ppm(3H, t, J=7.1 Hz), 1.29–1.37 ppm(4H, m), 1.30 ppm(3H, s), 1.33 ppm(3H, s), 1.51 ppm(3H, s), 1.58–1.62 ppm(2H, m), 2.62 ppm(3H, s), 2.83–3.04 ppm(2H, m), 2.91 ppm(1H, dd, J=11.7 Hz, 4.6 Hz), 3.10 ppm(1H, d, J=11.4 Hz), 3.14 ppm(1H, dd, J=11.4 Hz, 7.8 Hz), 3.23 ppm(1H, dd, J=11.7 Hz, 7.1 Hz), 3.40 ppm(1H, ddd, J=7.1 Hz, 6.6 Hz, 4.6 Hz), 3.45 ppm(1H, dd, J=11.4 Hz, 8.8 Hz), 3.51 ppm(1H, d, J=6.6 Hz), 3.61 ppm(1H, d, J=11.4 Hz), 3.77 ppm(3H, s), 4.18 ppm(1H, d, J=9.2 Hz), 4.35 ppm(1H, br), 4.76 ppm(1H, ddd, J=9.2 Hz, 8.8 Hz, 7.8 Hz, 6.70 ppm(1H, dd, J=7.6 Hz, 1.2 Hz) 6.85 ppm(1H, dd, J=8.3 Hz, 1.2 Hz), 7.20 ppm(1H, dd, J=8.3 Hz, 7.6 Hz), 12.86 ppm(1H, br). $^{13}$C-NMR(CDCl$_3$):14.04 ppm (q), 21.90 ppm(q), 22.48 ppm(t), 23.41 ppm (q), 26.07 ppm(q), 31.87 ppm(t), 32.18 ppm(t), 35.02 ppm(t), 35.42 ppm (t), 36.65 ppm(t), 41.25 ppm(t), 45.65 ppm(s), 45.89 ppm(q), 52.73 ppm (q), 73.02 ppm(d), 77.73 ppm(d), 78.06 ppm(d), 79.67 ppm(d), 83.69 ppm (s), 115.36 ppm(d), 116.25 ppm(s), 121.36 ppm(d), 132.15 ppm(d), 143.77 ppm(s), 159.69 ppm(s), 171.73 ppm(s), 173.72 ppm(s), 178.05 ppm (s).

Example 5

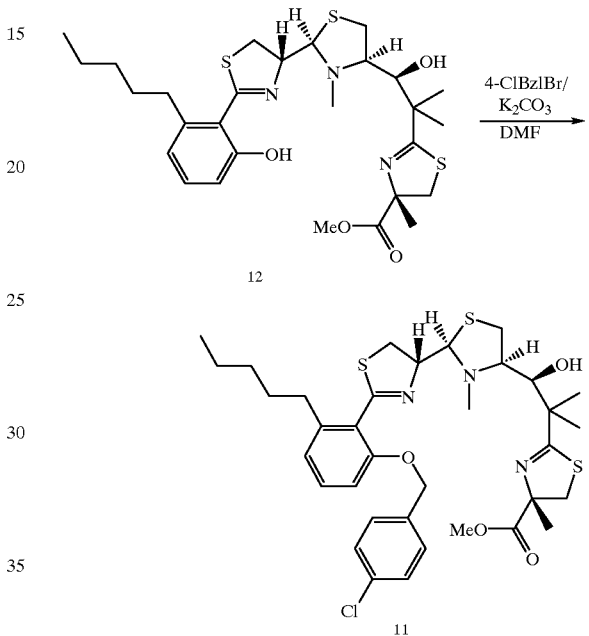

To a suspension consisting of 10.7 mg of compound 12, 50 mg of potassium carbonate and 190 μl of dimethylformamide, 5.0 mg of 4-chlorobenzylbromide was added at room temperature and then stirred for 2 hours. To the reaction was added dichloromethane, and the mixture was washed with an excessive amount of 5% potassium hydrogen sulfate solution. The organic layer was dried with anhydrous sodium sulfate, and then, the solvent was removed by evaporation in vacuo, and the resultant residue was subjected to silica gel column chlomatography (eluted consecutively with 20% ethyl acetate/hexane, 30% ethyl acetate/hexane)to give 10.7 mg of compound 11.

Molecular formula: $C_{35}H_{46}ClN_3O_4S_3$; $^1$H-NMR(CDCl$_3$): 0.89 (3H, t, J=7.1 Hz), 1.27 ppm(3H, s) 1.31 ppm(3H, s), 1.32–1.34 ppm(4H, m), 1.50 ppm(3H, s), 1.58–1.62 ppm (2H, m), 2.47 ppm(3H, s), 2.60–2.64 ppm(2H, m), 2.81 ppm(1H, dd, J=11.5 Hz, 3.7 Hz), 3.09 ppm(1H, d, J=11.2 Hz), 3.16 ppm(1H, dd, J=11.5 Hz, 7.1 Hz), 3.30 ppm(1H, ddd, J=7.1 Hz, 6.6 Hz, 3.7 Hz), 3.34 ppm(1H, dd, J=11.3 Hz, 7.1 Hz), 3.45 ppm(1H, d, J=6.6 Hz), 3.54 ppm(1H, dd, J=11.3 Hz, 8.8 Hz), 3.60 ppm(1H, d, J=11.2 Hz), 3.77 ppm(3H, s), 4.27 ppm(1H, d, J=8.8 Hz), 4.71 ppm(1H, br), 4.82 ppm(1H, dt, J=7.1 Hz, 8.8 Hz), 5.04 ppm(2H, s), 6.72 ppm(1H, d, J=7.6 Hz), 6.85 ppm(1H, d, J=7.1 Hz), 7.21 ppm(1H, dd, J=7.6 Hz, 7.1 Hz), 7.33 ppm(2H, d, J=8.5 Hz), 7.38 ppm(2H, d, J=8.5 Hz). $^{13}$C-NMR(CDCl$_3$): 14.04 ppm (q), 22.08 ppm(q), 22.54 ppm(t), 23.40 ppm ppm(q), 26.10 ppm(q), 30.88 ppm(t), 31.83 ppm(t), 32.85 ppm(t), 36.37 ppm ppm(t), 37.02 ppm(t), 41.26 ppm(t), 44.86 ppm(q), 45.67 ppm(s), 52.73 ppm ppm(q), 69.58 ppm(t), 72.25 ppm(d), 77.91 ppm(d), 79.49 ppm(d), 81.71 ppm (d), 83.61 ppm(s), 109.75 ppm(d), 121.99 ppm(d), 123.41 ppm(s), 128.49 ppm(d), 128.61 ppm(d), 129.95 ppm(d), 133.46 ppm(s), 135.60 ppm ppm(s), 142.79 ppm(s), 155.64 ppm(s), 166.41 ppm(s), 173.80 ppm(s), 178.00 ppm(s).

Example 6

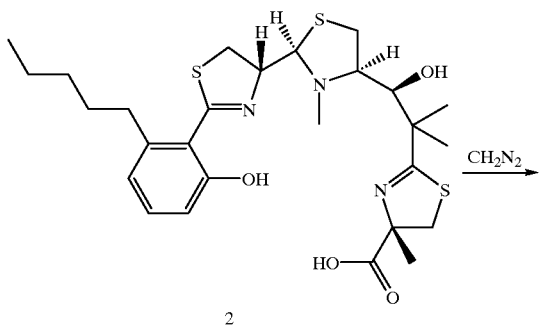

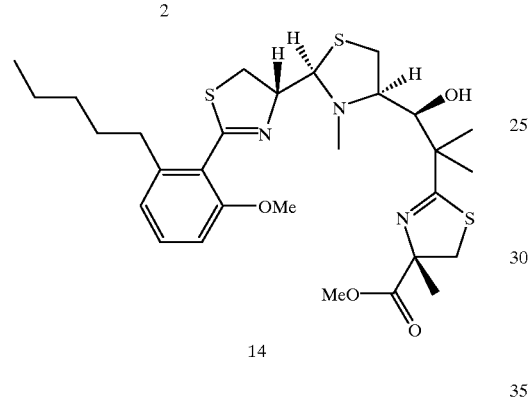

To 12 mg of compound 2 dissolved in 0.4 ml of methanol, a solution of diazomethane in ether was added and allowed to react at room temperature for 21 hours. After completion of the reaction, the mixture was concentrated to dryness in vacuo. Preparative TLC gave 12 mg of compound 14, which was further purified by preparative HPLC.

Molecular formula: $C_{29}H_{43}N_3O_4S_3$; FAB MS:m/z=616 [M+Na]$^+$, 594{M+H]$^+$; $^1$H-NMR(CDCl$_3$): 0.88 ppm(3H, t, J=7.1 Hz), 1.28 ppm(3H, s), 1.32 ppm(3H, s), 1.28–1.33 ppm(4H, m), 1.51 ppm(3H, s), 1.59–1.63 ppm(2H, m), 2.58–2.65 ppm(2H, m), 2.61 ppm(3H, s), 2.83 ppm(1H, dd, J=11.5 Hz, 3.6 Hz), 3.09 ppm(1H, d, J=11.2 Hz), 3.20 ppm(1H, dd, J=11.5 Hz, 7.1 Hz), 3.32 ppm(1H, m), 3.37 ppm(1H, dd, J=11.2 Hz, 7.3 Hz), 3.47 ppm(1H, d, J=6.6 Hz), 3.55 ppm(1H, dd, J=11.2 Hz, 8.7 Hz), 3.60 ppm(1H, d, J=11.2 Hz), 3.78 ppm(3H, s), 3.79 ppm(3H, s), 4.38 ppm (1H, d, J=8.3 Hz), 4.74 ppm(1H, br), 4.87 ppm(1H, ddd, J=8.7 Hz, 8.3 Hz, 7.3 Hz), 6.73 ppm(1H, d, J=8.3 Hz), 6.83 ppm(1H, d, J=7.6 Hz), 7.24 ppm(1H, dd, J=8.3 Hz, 7.6 Hz). $^{13}$C-NMR(CDCl$_3$): 13.99 ppm(q), 22.04 ppm(q), 22.50 ppm (t), 23.35 ppm (q), 26.04 ppm(q), 30.85 ppm(t), 31.78 ppm(t), 32.77 ppm(t), 36.30 ppm (t), 36.73 ppm(t), 41.21 ppm(t), 44.76 ppm(q), 45.61 ppm(s), 52.66 ppm (q), 55.80 ppm(q), 72.16 ppm(d), 77.86 ppm(d), 79.44 ppm(d), 81.56 ppm (d), 83.59 ppm(s), 108.35 ppm(d), 121.44 ppm(d), 122.75 ppm(s), 129.93 ppm(d), 142.55 ppm(s), 156.89 ppm (s), 166.38 ppm(s), 173.73 ppm (s), 177.98 ppm(s).

Example 7

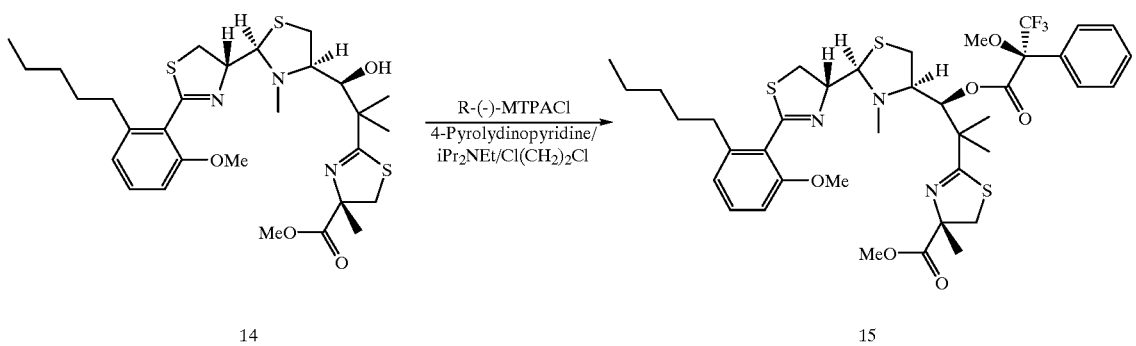

To 24.0 mg of compound 14 dissolved in 0.4 mL of 1, 2-dichloroethane, 8 mg of 4-pyrolydinopyridine and 10 μl of R-(−)-α-methoxy-α-(trifluoromethyl) phenylacethyl chloride (R-(−)-MTPAC1) were added and stirred at 55° C. After 30 minutes, 70μl of N,N-diisopropylethylamine and 10 μl of R-(-)-α-methoxy-α-(trifluoromethyl) phenylacethylchloride were added to the mixture, and stirred for 30 minutes. Ten µl of R-(-)-α-methoxy-α-(trifluoromethyl) phenylacethyl chloride was supplemented and stirred for 30 minutes. The reaction was further stirred at 70° C. for 1 hour and allowed to cool. The reaction was diluted with dichloromethane and then washed with an aqueous solution of 5% potassium hydrogen sulfate. The organic layer was dried with anhydrous sodium sulfate and the solvent was removed by evaporation in vacuo. The residue was dissolved in 1.0 ml of diethyl ether and 0.5 ml of methanol, and then, an exessive amount of trimethylsilyldiazomethane/hexane solution was added thereto and allowed to react. The reaction mixture was diluted with ethyl acetate and washed consecutively with an aqueous solution of 5% potassium hydrogen sulfate and saturated saline. The organic layer was dried with anhydrous sodium sulfate, and the solvent was removed in vacuo. The residue was subjected to silica gel column chromatography (eluted consecutively with 20% ethyl acetate/hexane and 50% ethyl acetate/hexane), and the aimed compound was further purified using HPLC to give 9.3 mg of compound 15.

Molecular formula: $C_{39}H_{50}F_3N_3O_6S_3$; $^1$H-NMR(CDCl$_3$: 0.86 ppm(3H, t, J=6.8 Hz), 1.19 ppm(3H, s), 1.24–1.30 (4H, m), 1.31 ppm(3H, s), 1.51 ppm(3H, s), 1.51–1.60 ppm(2H, m), 2.42 ppm(3H, s), 2.57–2.62 ppm(2H, m), 3.01 ppm(1H, dd, J=11.2 Hz, 6.3 Hz), 3.10 ppm(1H, dd, J=11.2 Hz, 7.8 Hz), 3.14 ppm(1H, d, J=11.4 Hz), 3.25 ppm(1H, ddd, J=7.8 Hz, 7.5 Hz, 6.3 Hz), 3.41 ppm (1H, dd, J=11.0 Hz, 9.1 Hz), 3.49 ppm(1H, dd, J=11.0 Hz, 9.3 Hz), 3.53 ppm(3H, s), 3.69 ppm(1H, d, J=11.4 Hz), 3.76 ppm(3H, s), 3.78 ppm(3H, s), 4.57 ppm(1H, d, J=5.9 Hz), 4.94 ppm(1H, ddd, J=9.3 Hz, 9.1 Hz, 5.9 Hz), 5.64 ppm(1H, d, J=7.5 Hz), 6.72 ppm(1H, d, J=7.8 Hz), 6.81 ppm(1H, d, J=7.1 Hz), 7.20–7.35 ppm(3H, m), 7.24 ppm (1H, dd, J=7.8 Hz, 7.1 Hz), 7.65 ppm(2H d, J=7.8 Hz) $^{13}$C-NMR(CDCl$_3$): 14.02 ppm(q), 21.05 ppm(q), 22.50 ppm(t), 23.25 ppm(q), 26.48 ppm(q), 31.04 ppm(t), 31.38 ppm(t), 32.88 ppm(t), 33.49 ppm(t), 35.94 ppm(t), 40.59 ppm(q), 41.70 ppm(t), 44.92 ppm(s), 52.85 ppm(d), 55.30 ppm(d), 55.93 ppm(d), 71.29 ppm(d), 78.37 ppm(d), 80.50 ppm(d), 80.77 ppm(d), 84.01 ppm(s), 84.92 ppm(q), 108.38 ppm(d), 121.51 ppm(d), 123.07 ppm(s), 123.45 ppm(q), 128.09 ppm(d), 128.40 ppm (d), 129.47 ppm(d), 129.82 ppm(d), 131.72 ppm(s), 142.76 ppm(s), 156.93 ppm (s), 165.97 ppm(s), 166.31 ppm(s), 173.37 ppm(s), 176.82 ppm (s).

7.0 µl of oxalyl chloride was dropped into a solution of 9.0 µl of dimethylsulfoxide in 0.4 ml of dichloromethane, while cooling with dry ice/acetone, with stirring. Then, a solution consisting of 23.1 mg of compound 14 and 0.4 ml of dichloromethane was dropped into the mixture, which was stirred for 30 minutes. Then, triethylamine was dropped into the solution. The temperature was gradually allowed to raise up to room temperature and the mixture was stirred for 30 minutes. Then, the reaction mixture was diluted with dichloromethane and washed with an aqueous solution of 5% potassium hydrogen sulfate. The organic layer was dried with anhydrous sodium sulfate and the solvent was removed by evaporation in vacuo. The residue was subjected to silica gel column chromatography (eluted consecutively with 30% ethyl acetate/hexane and 50% ethyl acetate/hexane, ethyl acetate of 10% methanol/ethyl acetate), which was repurified with silica gel column chromatography to give 4.0 mg of compound 16.

Molecular formula: $C_{29}H_{41}N_3O_4S_3$; $^1$H-NMR(CDCl$_3$): 0.88 ppm(3H, t, J=7.1 Hz), 1.32–1.37 ppm(4H, m), 1.46 ppm(3H, s), 1.51 ppm(3H, s), 1.54–1.62 ppm(2H, m), 1.56 ppm(3H, s), 2.40 ppm(3H, s), 2.62–2.67 ppm(2H, m), 2.81 ppm(1H, t, J=10.2 Hz), 3.06 ppm(1H, dd, J=10.2 Hz, 5.4 Hz), 3.18 ppm(1H, d, J=11.2 Hz), 3.49 ppm(1H, dd, J=11.0 Hz, 9.3 Hz), 3.74 ppm(1H, dd, J=11.0 Hz, 9.3 Hz), 3.75 ppm(1H, d, J=11.2 Hz), 3.80 ppm(3H, s), 3.81 ppm(3H, s), 4.11 ppm(1H, dd, J=10.2 Hz, 5.4 Hz), 4.66 ppm(1H, d, J=3.9 Hz), 5.16 ppm(1H, dt, J=3.9 Hz, 9.3 Hz), 6.72 ppm(1H, dd, J=8.3 Hz, 0.7 Hz), 6.82 ppm(1H, dd, J=7.8 Hz, 0.7 Hz), 7.23 ppm(1H, dd, J=8.3 Hz, 7.8 Hz). $^{13}$C-NMR(CDCl$_3$): 14.04 ppm, 22.56 ppm, 23.66 ppm, 23.93 ppm, 24.40 ppm, 31.14 ppm, 31.82 ppm, 32.85 ppm, 34.11 ppm, 34.54 ppm, 39.17 ppm, 42.00 ppm, 35.03 ppm, 54.27 ppm, 55.95 ppm, 73.36 ppm, 74.89 ppm, 79.79 ppm, 84.44 ppm, 108.31 ppm, 121.45 ppm, 122.82 ppm, 129.88 ppm, 142.75 ppm, 156.88 ppm, 167.15 ppm, 173.18 ppm, 174.21 ppm, 206.17 ppm.

Example 8

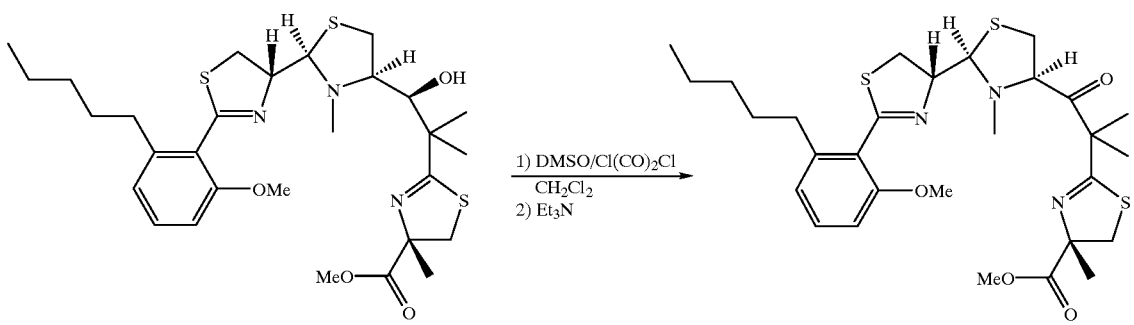

Example 9

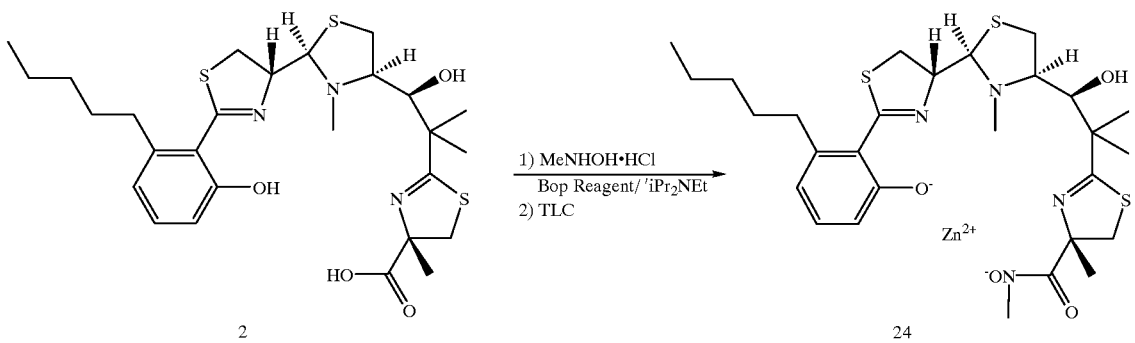

34.9 mg(77.7% contained)of compound 2 was dissolved in 1.0 ml of dimethylformamide, to which, while stirring under ice-cooling, 11 mg of N-methylhydroxylamine hydrochloride, 54 mg of BOP reagent (benzotriazol-1-yloxytrisppm(dimethylamino) phosphonium hexafluorophosphate) and 17 mg of N,N-diisopropylethylamine/10.0 ml of benzene were added, stirred for 15 minutes, and then, the mixture is allowed to react for 16 hours at room temperature. Water was added to the reaction, which was eluted with ethyl acetate. The solution was dried with anhydrous sodium sulfate, and dried in vacuo to give 58 mg of compound 24. The residue was purified by preparative TLC.

Molecular formula:$C_{28}H_{40}N_4O_4S_3Zn$; SIMS:m/z=657 [M+H]$^+$, 441; $^1$H-NMR(CDCl$_3$):0.91 ppm(3H, t, J=7.0 Hz), 1.34 ppm(3H, s), 1.34–1.37 ppm(4H, m), 1.54–1.57 ppm (2H, m), 1.57 ppm(3H, s), 1.64 ppm(3H, s), 2.30 ppm(1H, m), 2.31 ppm(3H, s), 2.78 ppm(1H, dd, J=12.5 Hz, 7.1 Hz), 2.92 ppm(3H, s), 3.01–3.05 ppm(3H, m), 3.19ppm (1H, m), 3.57 ppm(1H, m), 3.58 ppm(1H, d, J=12.6 Hz), 3.59 ppm (1H, m), 3.74 ppm(1H, d, J=12.6 Hz), 3.94 ppm(1H, d, J=10.8 Hz), 4.44 ppm (1H, dt, J=10.8 Hz, 9.8 Hz), 6.61 ppm(1H, d, J=7.0 Hz), 6.62 ppm(1H, d, J=7.0 Hz), 7.16 ppm(1H, t, J=7.0 Hz), 11.68 ppm(1H, br). $^{13}$C-NMR (CDCl$_3$):14.18 ppm, 20.75 ppm, 22.55 ppm, 25.38 ppm, 29.41 ppm, 31.52 ppm, 33.19 ppm, 35.56 ppm, 35.74 ppm, 37.31 ppm, 37.75 ppm, 38.24 ppm, 45.28 ppm, 47.83 ppm, 72.16 ppm, 74.86 ppm, 77.59 ppm, 81.13 ppm, 83.45 ppm, 119.25 ppm, 120.68 ppm, 121.26 ppm, 133.50 ppm, 145.80 ppm, 165.95 ppm, 171.59 ppm, 173.64 ppm, 187.38 ppm.

Example 10

21 mg (0.03 mM) of compound 2 was dissolved in 1.0 ml of dimethylformamide, to which, while stirring under ice-cooling, 13 mg (0.16 mM) of N-methylhydroxylamine hydrochloride and 57 mg (0.13 mM) of BOP reagent were added. After stirring for 10 minutes at the same temperature, a solution of 21 mg (0.16 mM) of N,N-diisopropylethylamine in 1 ml of benzene was added to the reaction, and the mixture was stirred for 15 minutes, and then, stirred for 2 days at room temperature. To the reaction was added water, and the mixture was extracted with ethyl acetate, washed with water, dried with anhydrous sodium sulfate, and the solvent was removed by evaporation to obtain 36 mg of a partially purified product of compound 25. Isolation and purification by using HPLC gave the aimed compound.

Molecular formula: $C_{28}H_{42}N_4O_4S_3$; SIMS:m/z=617[M+Na]$^+$, 595[M+H]$^+$, 379, 346, 248, 245

Example 11

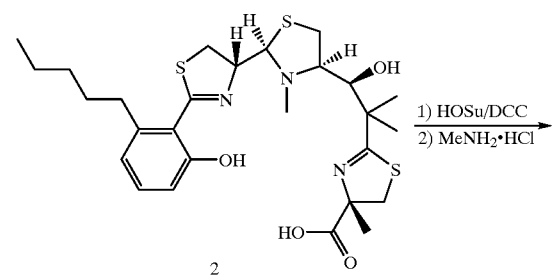

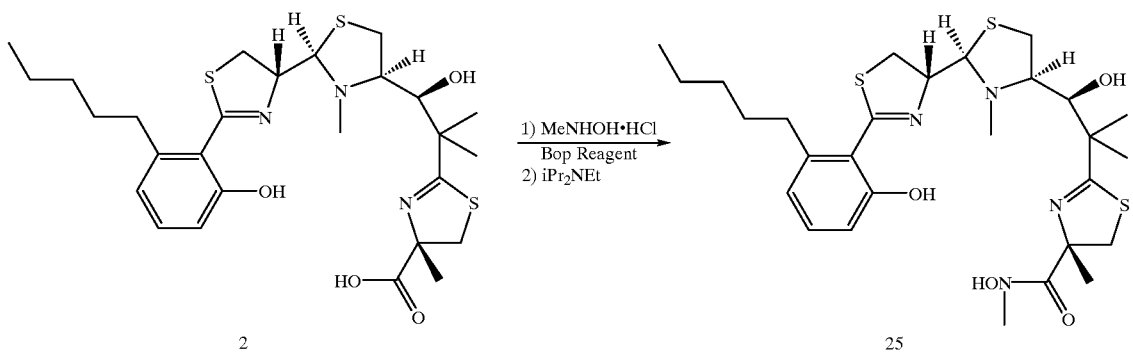

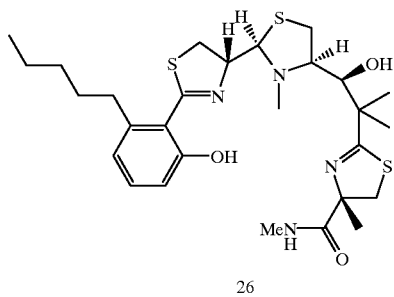

25 mg of compound 2 was dissolved in 0.5 ml of dimethylformamide. 5.5 mg of N-hydroxysuccinimide and 9.9 mg of 1,3-dicyclohexylcarbodiimide were added to the mixture under ice-cooling, followed by stirring for 1 hour. Methylamine hydrochloride (14.6 mg)/dimethylformamide (1.0 ml) was added to the reaction, which was stirred for 1 hour under ice-cooling and then for 16 hours at room temperature. Water was added to the reaction, which was extracted with ethyl acetate. The extract was purified by using preparative TLC to give 30 mg of compound 26, which was further purified by preparative HPLC.

Molecular formula: $C_{28}H_{42}N_4O_4S_3$; SIMS:m/z=579[M+H]$^+$; $^1$H-NMR(CDCl$_3$):0.90 ppm(3H, t, J=7.1 Hz), 1.30 ppm(3H, s), 1.30 ppm(3H, s), 1.30–1.38 ppm(4H, m), 1.51 ppm(3H, s), 1.57–163 ppm (2H, m), 2.63 ppm(3H, s), 2.80 ppm(3H, d, J=4.9 Hz), 2.87–3.03 ppm (2H, m), 2.95 ppm (1H, dd, J=11.5 Hz, 4.4 Hz), 3.14 ppm(1H, dd, J=11.5 Hz, 7.3 Hz), 3.15 ppm(1H, d, J=11.5 Hz), 3.24 ppm(1H, dd, J=11.5 Hz, 7.3 Hz), 3.35 ppm(1H, ddd, J=7.3 Hz, 7.1 Hz, 4.4 Hz), 3.48 ppm(1H, dd, J=11.5 Hz, 8.8 Hz), 3.56 ppm(1H, d, J=11.5 Hz), 3.68 ppm(1H, d, J=7.1Hz), 4.19 ppm(1H, d, J=9.5 Hz), 4.42 ppm(1H, br), 4.74 ppm(1H, ddd, J=9.5 Hz, 8.8 Hz, 7.3 Hz), 6.71 ppm(1H, dd, J=7.6 Hz, 1.0 Hz), 6.84 ppm(1H, dd, J=8.1 Hz, 1.0 Hz), 6.96 ppm(1H, br), 7.21 ppm(1H, dd, J=8.1 Hz, 7.6 Hz), 12.83 ppm(1H, br). $^{13}$C-NMR(CDCl$_3$):14.05 ppm(q), 22.49 ppm(t), 23.51 ppm(q), 24.17 ppm (q), 24.83 ppm(q), 26.14 ppm(q), 31.87 ppm(t), 32.20 ppm(t), 35.16 ppm (t), 35.44 ppm(t), 36.85 ppm(t), 41.52 ppm(t), 45.42 ppm(s), 46.27 ppm (q), 72.98 ppm(d), 78.10 ppm(d), 78.15 ppm(d), 78.15 ppm(d) 79.47 ppm (d), 84.31 ppm(s), 115.39 ppm(d), 116.19 ppm(s), 121.44 ppm (d), 132.27 ppm(d), 143.82 ppm(s), 159.72 ppm(s), 171.99 ppm(s), 175.26 ppm(s), 179.36 ppm(s)

Example 12

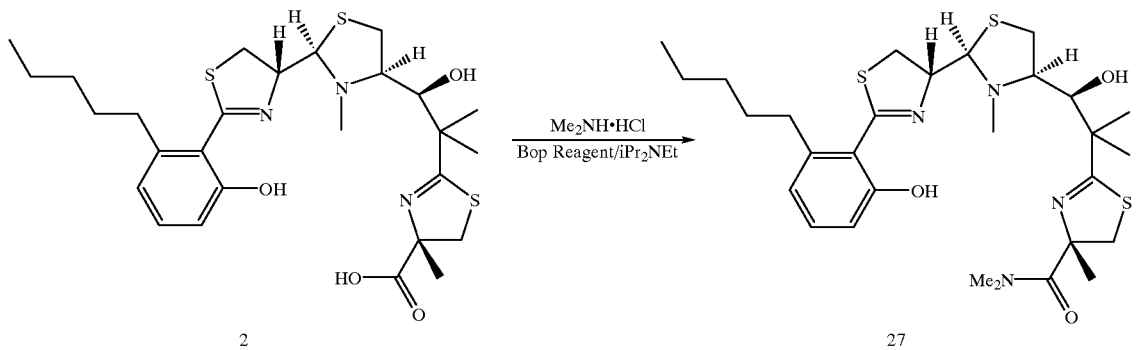

35 mg of compound 2 was dissolved in 1.0 ml of dimethylformamide. 10.6 mg of dimethylamine hydrochloride and 57 mg of BOP reagent were added to the mixture with stirring on ice. N,N-diisopropylethylamine (17 mg)/benzene (1.0 ml) was then added to the reaction, stirred for 15 minutes at the same temperature and then for 24 hours at room temperature. To the reaction was added water, and the mixture was extracted with ethyl acetate. The extract was subjected to preparative TLC to give compound 27 (15.5 mg), and the mixture was further purified by preparative HPLC.

Molecular formula: $C_{29}H_{44}N_4O_4S_3$; SIMS:m/z=593[M+H]$^+$, 379,344

Example 13

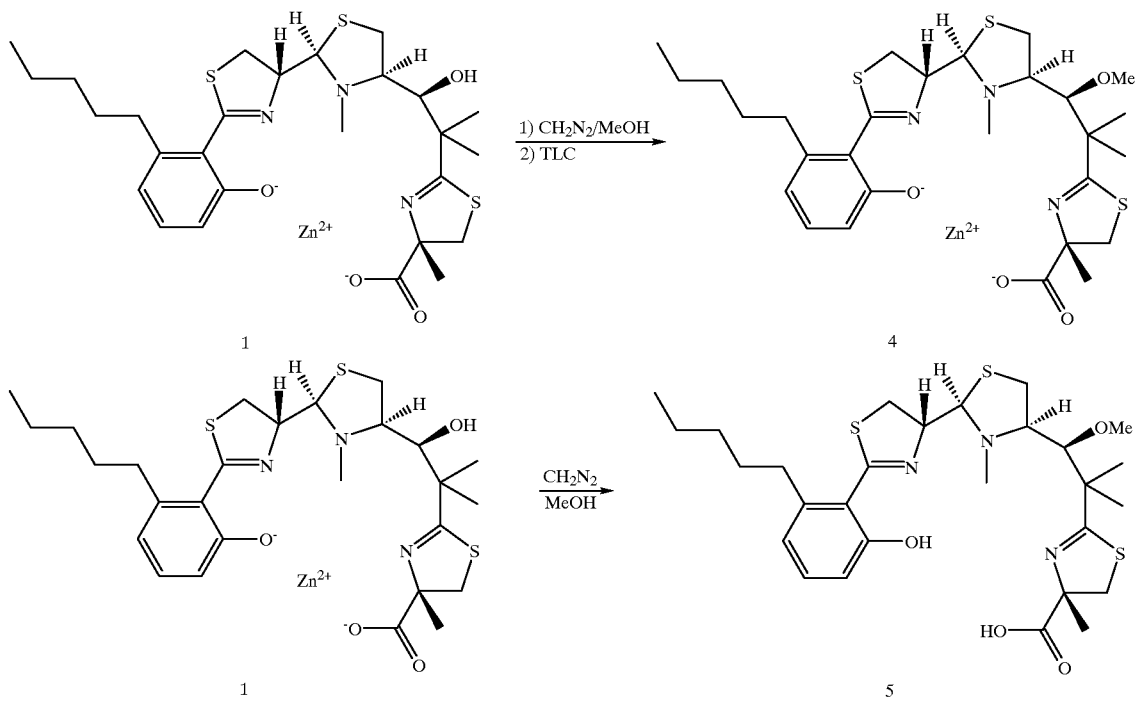

54 mg of compound 1 was dissolved in 7 ml of methanol. To the mixture, a solution of diazomethane in ether was added, and the mixture was allowed to react for 1 hour at room temperature. After the reaction, the reaction mixture was concentrated to dryness in vacuo, which was isolated and purified by using preparative TLC and preparative HPLC to give compound 4 (7.6 mg) and 5 (5.0 mg).

Compound 4:

Molecular formula: $C_{28}H_{39}N_3O_4S_3Zn$; SIMS m/z=664 [M+Na]$^+$, 642[M+H]$^+$;

Compound 5:

Molecular formula: $C_{28}H_{41}N_3O_4S_3$; FAB MS m/z=580 [M+H]$^+$; $^1$H-NMR(CDCl$_3$):0.90 ppm(3H, t, J=7.1 Hz), 1.28 ppm(3H, s), 1.30 ppm(3H, s), 1.32–1.39 ppm(4H, m), 1.53 ppm(3H, s), 1.59–1.67 ppm (2H, m), 2.64 ppm(3H, s), 2.92–3.02 ppm(4H, m), 3.13 ppm(1H, m), 3.21 ppm(1H, d, J=11.7 Hz), 3.22 ppm(1H, dd, J=11.2 Hz, 8.8 Hz), 3.37 ppm(1H, d, J=7.8 Hz), 3.40 ppm(1H, dd, J=11.2 Hz, 8.8 Hz), 3.62 ppm(1H, d, J=11.7 Hz), 4.15 ppm(1H, d, J=8.1 Hz), 4.75 ppm(1H, dt, J=8.1 Hz, 8.8 Hz), 6.70 ppm(1H, dd, J=7.6 Hz, 1.2 Hz), 6.84 ppm (1H, dd, J=8.3 Hz, 1.2 Hz), 7.20 ppm(1H, dd, J=8.3 Hz, 7.6 Hz). $^{13}$C-NMR(CDCl$_3$):14.06 ppm, 22.48 ppm, 22.51 0ppm, 23.66 ppm, 26.04 ppm, 31.92 ppm, 32.34 ppm, 34.67 ppm, 34.86 ppm, 35.55 ppm, 40.62 ppm, 45.50 ppm, 46.61 ppm, 61.96 ppm, 74.59 ppm, 78.55 ppm, 78.92 ppm, 83.71 ppm, 90.43 ppm, 115.49 ppm, 116.02 ppm, 121.34 ppm, 132.15 ppm, 143.85 ppm, 160.38 ppm, 171.68 ppm, 174.67 ppm, 181.71 ppm.

Example 14

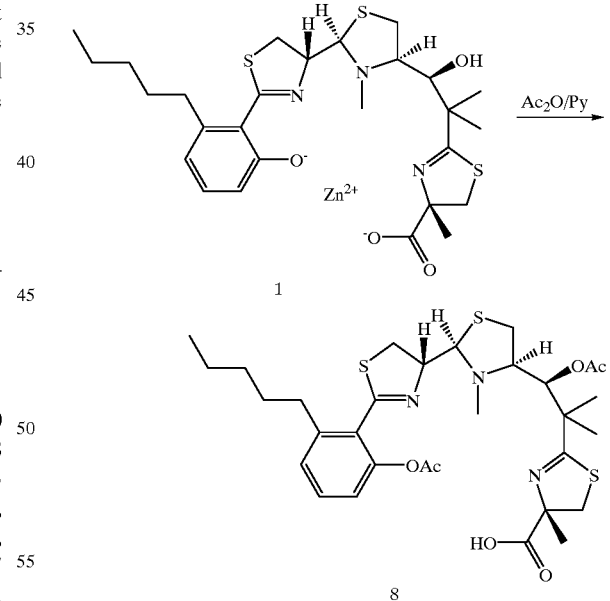

199 mg of compound 1 was dissolved in pyridine, and to the mixture, anhydrous acetic acid (2.5 ml) was added, and the mixture was allowed to react for 16 hours at room temperature, and then, dried in vacuo. Then, compound 8 (16 5 mg) was obtained by using preparative TLC, which was further purified by using preparative HPLC.

Molecular formula: $C_{31}H_{43}N_3O_6S_3$; SIMS:m/z=672[M+Na]$^+$, 650[M+H]$^+$; $^1$H-NMR(CDCl$_3$):0.88 ppm(3H, t, J=7.1 Hz), 1.32 ppm(6H, s), 1.32–1.35 ppm(4H, m), 1.51 ppm(3H, s), 1.58–1.62 ppm(2H, m), 2.09 ppm(3H, s), 2.29 ppm(3H, s), 2.57 ppm(3H, s), 2.64–2.68 ppm(2H, m), 2.97–3.06 ppm(2H, m), 3.20 ppm(1H, m), 3.21 ppm(1H, d, J=11.7 Hz), 3.37 ppm(1H, dd, J=11.2 Hz, 8.8 Hz), 3.49 ppm(1H, dd, J=11.2 Hz, 9.8 Hz), 3.63 ppm(1H, d, J=11.7 Hz), 4.50 ppm(1H, d, J=5.6 Hz), 4.90 ppm(1H, ddd, J=9.8 Hz, 8.8 Hz, 5.6 Hz), 5.30 ppm(1H, d, J=6.3 Hz), 6.94 ppm(1H, dd, J=8.0 Hz, 1.2 Hz), 7.10 ppm(1H, dd, J=7.8 Hz, 1.2 Hz), 7.31 ppm(1H, dd, J=8.0 Hz, 7.8 Hz).

Example 15

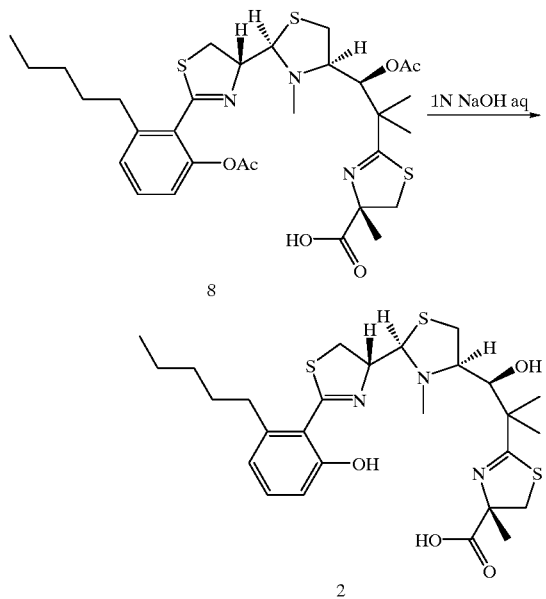

Compound 8 (145 mg) was dissolved in methanol (6 ml), and to the mixture an aqueous solution of 1 N sodium hydroxide (3 ml) was added with cooling, and the mixture was allowed to react for 16 hours at room temperature. The reaction was neutralized with 6 N hydrochloric acid with cooling and methanol was concentrated in vacuo. To the residue, saturated saline was added and extracted with ethyl acetate. The reaction was dried over anhydrous sodium sulfate and evaporated in vacuo to give compound 2 (109 mg), which was purified by using preparative HPLC.

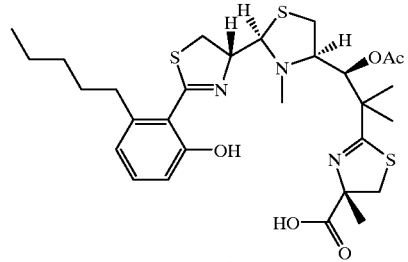

Compound 8 (22 mg) was dissolved in methanol (3 ml), and to the mixture, 0.5 N sodium hydroxide was added with stirring on ice followed by stirring for 15 minutes. The reaction was adjusted to pH 6 by 0.5 N hydrochloric acid under ice-cooling, and the methanol was evaporated in vacuo. To the concentrate was added water, and the resultant mixture was extracted with dichloromethane, washed with water, dried over anhydrous sodium sulfate, and then, the solvent was removed by evaporation to give 21 mg of compound 3. For a sample for identifying structure and assay, the compound was further purified by using HPLC.

SIMS m/z=608[M+H]$^+$; $^1$H-NMR(CDCl$_3$):0.90 ppm(3H, t, J=7.2 Hz), 1.33 ppm(3H, s), 1.35 ppm(3H, s), 1.35–1.39 ppm(4H, m), 1.52 ppm(3H, s), 1.60–1.64 ppm (2H, m), 2.16 ppm(3H, s), 2.58 ppm(3H, s), 2.89–3.04 ppm(2H, m), 3.04 ppm(1H, dd, J=11.7 Hz, 7.6 Hz), 3.09 ppm(1H, dd, J=11.7 Hz, 7.1 Hz), 3.16 ppm(1H, dd, J=11.2 Hz, 8.3 Hz), 3.23 ppm(1H, d, J=11.5 Hz), 3.30 ppm(1H, ddd, J=7.6 Hz, 7.1 Hz, 6.8 Hz), 3.36 ppm (1H, dd, J=11.2 Hz, 8.8 Hz), 3.65 ppm(1H, d, J=11.5 Hz), 4.16 ppm (1H, d, J=8.5 Hz), 4.78 ppm(1H, ddd, J=8.8 Hz, 8.5 Hz, 8.3 Hz), 5.36 ppm(1H, d, J=6.8 Hz), 6.69 ppm(1H, dd, J=7.6 Hz, 1.2 Hz), 6.83 ppm(1H, dd, J=8.3 Hz, 1.2 Hz), 7.19 ppm(1H, dd, J=8.3 Hz, 7.6 Hz). $^{13}$NMR(CDCl$_3$):14.06 ppm(q), 21.05 ppm(q), 22.52 ppm(t ), 23.34 ppm(q), 23.72 ppm(q), 24.87 ppm(q), 31.92 ppm(t), 32.30 ppm(t), 34.61 ppm(t), 35.40 ppm(t), 35.50 ppm(t), 40.78 ppm(t), 44.76 ppm(q), 44.95 ppm(s), 71.86 ppm(d), 77.95 ppm(d), 78.73 ppm(d), 78.89 ppm(d), 83.89 ppm(s), 115.45 ppm(d), 116.14 ppm(s), 121.24 ppm (d), 132.02 ppm (d), 143.89 ppm(s), 160.30 ppm(s), 170.53 ppm(s), 171.45 ppm(s), 174.73 ppm(s), 180.51 ppm(s).

Example 16

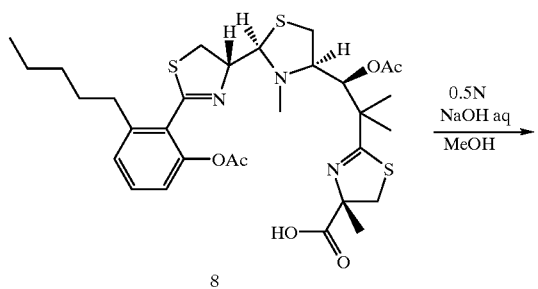

Example 17

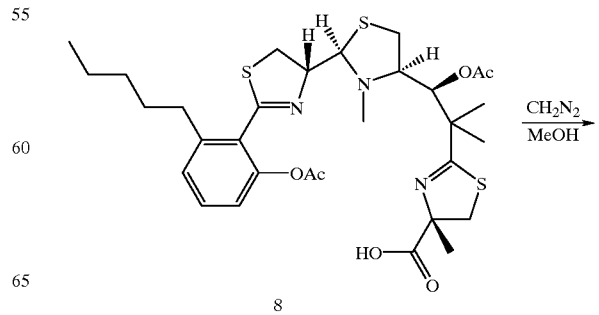

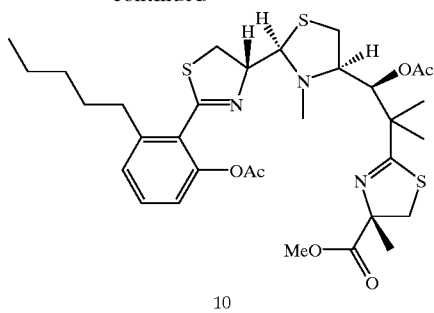

10

Compound 8 (3.6 mg) was dissolved in methanol (1.0 ml), and to the solution was added a solution of diazomethane in ether. After 30 minutes at room temperature, the reaction was concentrated to dryness, and the residue was purified by using preparative HPLC to give compound 10 (2.4 mg).

Molecular formula:$C_{32}H_{45}N_3O_6S_3$; SIMS:m/z=664[M+H]$^+$; $^1$H-NMR(CDCl$_3$):0.89 ppm(3H, t, J=7.0 Hz), 1.31–1.34 ppm(4H, m), 1.34 ppm(6H, s), 1.54 ppm(3H, s), 1.59–1.61 ppm(2H, m), 2.10 ppm(3H, s), 2.29 ppm(3H, s), 2.56 ppm(3H, s), 2.65–2.69 ppm(2H, m), 3.01 ppm (1H, dd, J=11.5 Hz, 6.8 Hz), 3.04 ppm(1H, dd, J=11.5 Hz, 6.8 Hz), 3.12 ppm(1H, d, J=11.2 Hz), 3.21 ppm(1H, q, J=6.8 Hz), 3.37 ppm(1H, dd, J=11.2 Hz, 9.0 Hz), 3.51 ppm(1H, dd, J=11.2 Hz, 10.0 Hz), 3.67 ppm(1H, d, J=11.2 Hz), 3.78 ppm(3H, s), 4.52 ppm(1H, d, J=5.4 Hz), 4.90 ppm(1H, ddd, J=10.0 Hz, 9.0 Hz, 5.4 Hz), 5.21 ppm(1H, d, J=6.3 Hz), 6.94 ppm(1H, dd, J=8.1 Hz, 1.0 Hz), 7.10 ppm(1H, dd, J=7.6 Hz, 1.0 Hz), 7.30 ppm(1H, dd, J=8.1 Hz, 7.6 Hz).

Example 18

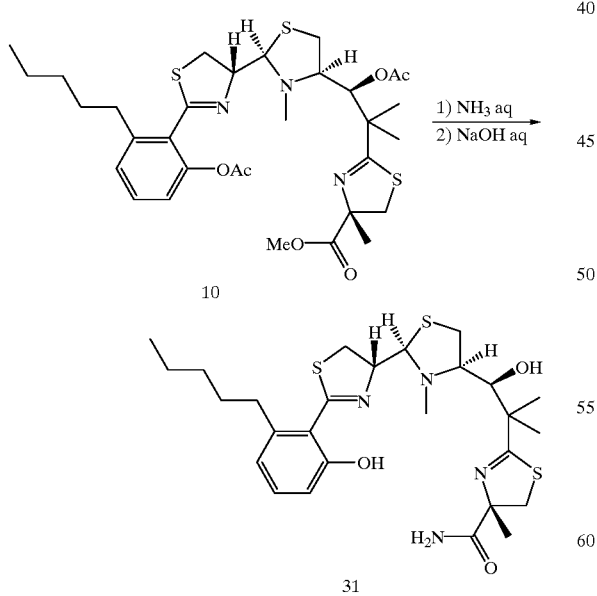

To compound 10 (21 mg) dissolved in methanol (0.5 ml), 28% aqueous ammonia solution (60 mg) was added at room temperature, and left to stand for 17 hours at the same temperature, and then, 28% aqueous ammonia solution (60 mg) was added thereto, and left to stand for 24 hours. 1N-sodium hydroxide (0.3 ml) was added to the reaction at room temperature, and then, stirred for 5 hours. The reaction was neutralized with 0.5 N hydrochloric acid. After water was added thereto, the mixture was extracted with dichloromethane, washed with water, dried over anhydrous sodium sulfate, and the solvent was removed by evaporation to give a crude product of compound 31 (17 mg). A sample for identifying structure and assay was obtained by further purification using preparative HPLC.

Molecular formula:$C_{27}H_{40}N_4O_3S_3$; FAB MS:m/z=587 [M+Na]$^+$, 565[M+H]$^+$, 379, 349, 316

Example 19

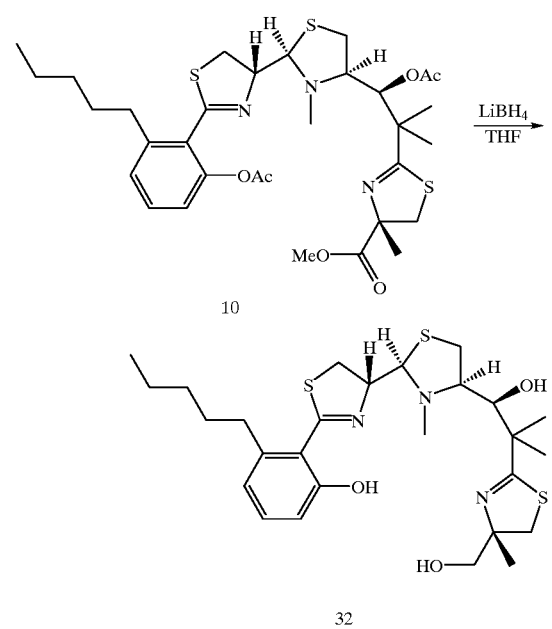

32

To a solution of compound 10 (23 mg) in anhydrous tetrahydrofurane (0.5 ml) was added a solution of lithium borohydride (5 mg ) in anhydrous tetrahydrofurane with stirring on ice. The mixture was stirred for 10 minutes at room temperature. 3 mg of lithium borohydride was added thereto under ice-cooling, and the mixture was stirred for 2 hours at room temperature. Acetone and water were added to the reaction, and the mixture was neutralized with 0.5 N hydrochloric acid, eluted with ethyl acetate, washed with water, dried over anhydrous sodium sulfate, and then, the solvent was removed by evaporation. The residue was subjected to preparative TLC to give 9 mg of compound 32, which was further purified by HPLC and the structure thereof was identified.

Molecular formula: $C_{27}H_{41}N_3O_3S_3$; SIMS:m/z=574[M+Na]$^+$, 552[M+H]$^+$, 379,349,303,248

Example 20

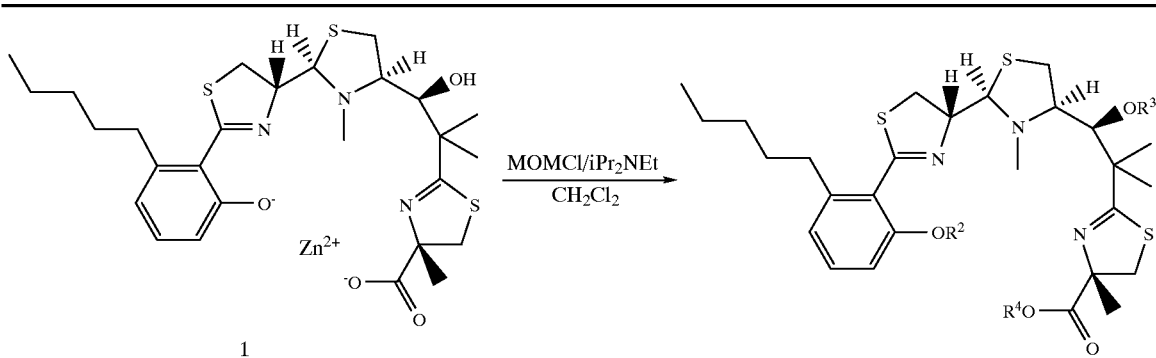

| Compound No. | R⁴ | R² | R³' |
|---|---|---|---|
| 17 | Methoxymethyl | Methoxymethyl | Methoxymethyl |
| 18 | Methoxymethyl | Methoxymethyl | H |
| 19 | Methoxymethyl | H | Methoxymethyl |
| 20 | Methoxymethyl | H | H |

To compound 1 (50 mg) dissolved in dichloromethane, N,N-diisopropylethylamine (17 μl) and chloromethyl methyl ether (MOMCl) (7.0 μl) were added and the mixture was stirred for 5 hours. The reaction mixture was poured into ice water containing potassium hydrogen sulfate, and extracted with dichloromethane. The organic layer was washed with saturated saline, dried over anhydrous sodium sulfate, and the solvent was removed by evaporation in vacuo. The residue was subjected to silica gel column chromatography (eluted consecutively with 20–50% ethyl acetate hexane, ethyl acetate and 10–20% methanol/ethyl acetate) for purification. After further repurification with HPLC, compound 17 (18.0 mg) compound 18 (14.2 mg), compound 19 (1.9 mg) and compound 20 (5.8 mg) were obtained.

Compound 17:

Molecular formula: $C_{33}H_{51}N_3O_7S_3$; $^1$H-NMR(CDCl$_3$): 0.88 ppm(3H, t, J=7.1 Hz), 1.32 ppm(3H, s), 1.32–1.34 ppm(4H, m), 1.34 ppm(3H, s), 1.54 ppm(3H, s), 1.58–1.65 ppm(2H, m), 2.57–2.69 ppm(2H, m), 2.60 ppm(3H, s), 2.90 ppm(1H, dd, J=11.2 Hz, 8.3 Hz), 3.03 ppm(1H, dd, J=11.2 Hz, 6.4 Hz), 3.10 ppm(1H, m), 3.11 ppm(1H, d, J=11.5 Hz), 3.41 ppm(1H, dd, J=10.7 Hz, 8.8 Hz), 3.42 ppm(3H, s), 3.47 ppm(3H, s), 3.48 ppm(3H, s), 3.55 ppm(1H, dd, J=10.7 Hz, 9.8 Hz), 3.66 ppm(1H, d, J=11.5 Hz), 3.88 ppm(1H, d, J=6.6 Hz), 4.49 ppm(1H, d, J=5.4 Hz), 4.73 ppm(1H, d, J=6.6 Hz), 4.98 ppm(1H, ddd, J=9.8 Hz, 8.8 Hz, 5.4 Hz), 5.00 ppm (1H, d, J=6.6 Hz), 5.14 ppm(1H, d, J=6.6 Hz), 5.19 ppm(1H, d, J=6.6 Hz), 5.29 ppm(1H, d, J=5.9 Hz), 5.35 ppm(1H, d, J=5.9 Hz), 6.87 ppm(1H, d, J=7.8 Hz), 6.94 ppm(1H, d, J=7.8 Hz), 7.21 ppm(1H, t, J=7.8 Hz).

Compound 18:

Molecular formula: $C_{31}H_{47}N_3O_6S_3$; $^1$H-NMR(CDCl$_3$): 0.89 ppm(3H, t, J=7.0 Hz), 1.28 ppm(3H, s) 1.28–1.34 ppm(4H, m), 1.32 ppm(3H, s), 1.54 ppm(3H, s), 1.59–1.63 ppm(2H, m), 2.61 ppm(3H, s), 2.61–2.65 ppm(2H, m), 2.84 ppm(1H, dd, J=11.7 Hz, 3.7 Hz), 3.10 ppm(1H, d, J=11.5 Hz), 3.22 ppm(1H, dd, J=11.7 Hz, 6.8 Hz), 3.34 ppm(1H, m), 3.36 ppm(1H, dd, J=11.2 Hz, 7.8 Hz), 3.47 ppm(1H, d, J=7.1 Hz), 3.47 ppm(3H, s), 3.48 ppm(3H, s), 3.55 ppm(1H, dd, J=11.2 Hz, 8.8 Hz), 3.64 ppm(1H, d, J=11.5 Hz), 4.37 ppm(1H, d, J=8.5 Hz), 4.74 ppm(1H, br), 4.86 ppm(1H, ddd, J=8.8 Hz, 8.5 Hz, 7.8 Hz), 5.16 ppm(2H, s), 5.29 ppm(1H, d, J=5.9 Hz), 5.35 ppm(1H, d, J=5.9 Hz), 6.88 ppm(1H, d, J=7.8 Hz), 6.95 ppm(1H, d, J=7.8 Hz), 7.23 ppm(1H, t, J=7.8 Hz).

Compound 19:

Molecular formula: $C_{31}H_{47}N_3O_6S_3$; $^1$H-NMR(CDCl$_3$): 0.90 ppm(3H, t, J=7.1 Hz), 1.33 ppm(3H, s) 1.34 ppm(3H, s), 1.34–1.37 ppm(4H, m), 1.52 ppm(3H, s), 1.57–1.62 ppm(2H, m), 2.61 ppm(3H, s), 2.92–3.01 ppm(3H, m), 3.09 ppm(1H, dd, J=11.7 Hz, 6.8 Hz), 3.12 ppm(1H, d, J=11.5 Hz), 3.19 ppm(1H, dd, J=11.2 Hz, 8.8 Hz), 3.20 ppm(1H, m), 3.38 ppm(1H, dd, J=11.2 Hz, 8.8 Hz), 3.44 ppm(3H, s), 3.49 ppm(3H, s),3.68 ppm(1H, d, J=11.5 Hz), 3.83 ppm(1H, d, J=7.6 Hz), 4.14 ppm(1H, d, J=8.5 Hz), 4.77 ppm(1H, dt, J=8.5 Hz, 8.8 Hz), 4.83 ppm(1H, d, J=6.6 Hz), 5.07 ppm(1H, d, J=6.6 Hz), 5.28 ppm(1H, d, J=6.1 Hz), 5.36 ppm(1H, d, J=6.1 Hz), 6.69 ppm(1H, d, J=7.3 Hz), 6.84 ppm(1H, d, J=7.0 Hz), 7.19 ppm(1H, dd, J=7.3 Hz, 7.0 Hz), 13.35 ppm(1H, br).

Compound 20:

Molecular formula: $C_{29}H_{43}N_3O_5S_3$; $^1$H-NMR(CDCl$_3$): 0.90 ppm(3H, t, J=7.1 Hz), 1.31 ppm(3H, s) 1.34 ppm(3H, s), 1.34–1.38 ppm(4H, m), 1.55 ppm(3H, s), 1.55–1.63 ppm(2H, m), 2.63 ppm(3H, s), 2.86–3.04 ppm(2H, m), 2.93 ppm(1H, dd, J=11.7 Hz, 4.4 Hz), 3.13 ppm(1H, d, J=11.5 Hz), 3.14 ppm(1H, dd, J=11.5 Hz, 8.1 Hz), 3.26 ppm(1H, dd, J=11.7 Hz, 7.1 Hz), 3.42 ppm(1H, ddd, J=7.1 Hz, 6.6 Hz, 4.4 Hz), 3.46 ppm(1H, dd, J=11.5 Hz, 8.8 Hz), 3.48 ppm(3H, s), 3.52 ppm(1H, d, J=6.6 Hz), 3.66 ppm(1H, d, J=11.5 Hz), 4.19 ppm(1H, d, J=9.5 Hz), 4.38 ppm(1H, br), 4.77 ppm(1H, ddd, J=9.5 Hz, 8.8 Hz, 8.1 Hz), 5.30ppm(1H, d, J=5.9 Hz), 5.35 ppm (1H, d, J=5.9 Hz),6.70 ppm(1H, dd, J=7.6 Hz, 1.2 Hz), 6.85 ppm(1H, dd, J=8.3 Hz, 1.2 Hz), 7.21 ppm(1H, ddr J=8.3 Hz, 7.6 Hz), 12.84 ppm (1H, br).

Example 21

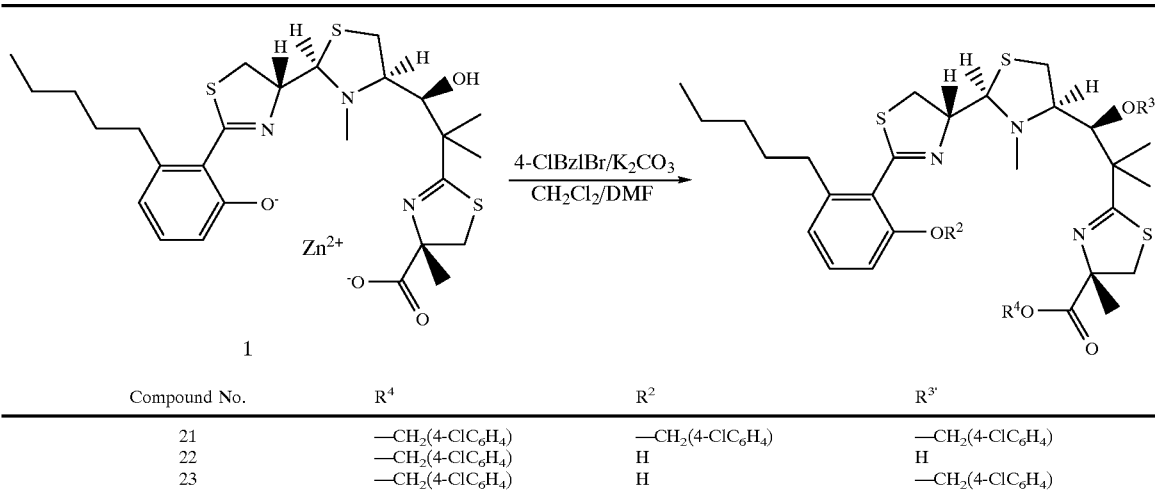

| Compound No. | $R^4$ | $R^2$ | $R^{3'}$ |
|---|---|---|---|
| 21 | —CH$_2$(4-ClC$_6$H$_4$) | —CH$_2$(4-ClC$_6$H$_4$) | —CH$_2$(4-ClC$_6$H$_4$) |
| 22 | —CH$_2$(4-ClC$_6$H$_4$) | H | H |
| 23 | —CH$_2$(4-ClC$_6$H$_4$) | H | —CH$_2$(4-ClC$_6$H$_4$) |

To a suspension consisting of compound 1 (5 0 mg), potassium carbonate (220 mg), dichloromethane (80 μl), dimethylformamide (400 μl) was added 4-chlorobenzylbromide (35 mg) at room temperature, and the mixture was stirred for 20 hours. Dichloromethane was added to the reaction mixture, and the mixture was consecutively washed with an aqueous solution of 5% potassium hydrogen sulfate and saturated saline. The organic layer was dried over anhydrous sodium sulfate and the solvent was removed by evaporation in vacuo. The resultant residue was subjected to silica gel column chromatography (eluted consecutively with 20%–80% ethyl acetate/hexane and ethyl acetate), and the partially purified compound was repurified by using HPLC to give compound 21 (7.2 mg), compound 22 (6.0 mg) and compound 23 (2 3.2 mg).

Compound 21:

Molecular formula: C$_{48}$H$_{54}$Cl$_3$N$_3$O$_4$S$_3$; $^1$H-NMR (CDCl$_3$): 0.87 ppm(3H, t, J=7.1 Hz), 1.26 ppm(3H, s), 1.30 ppm(3H, s), 1.30–1.33 ppm(4H, m), 1.50 ppm(3H, s), 1.59–1.61 ppm(2H, m), 2.51 ppm(3H, s), 2.64 ppm(2H, dd, J=9.3 Hz, 6.6 Hz), 2.90 ppm(1H, dd, J=11.4 Hz, 8.5 Hz), 3.02 ppm(1H, dd, J=11.4 Hz, 6.5 Hz), 3.06 ppm(1H, d, J=11.2 Hz), 3.11 ppm(1H, ddd, J=8.3 Hz, 7.6 Hz, 6.5 Hz), 3.42 ppm(1H, dd, J=10.8 Hz, 8.5 Hz), 3.53 ppm(1H, dd, J=10.8 Hz, 9.0 Hz), 3.59 ppm(1H, d, J=11.2 Hz), 3.71 ppm(1H, d, J=7.6 Hz), 4.39 ppm(1H, d, J=6.4 Hz), 4.44 ppm(1H, d, J=11.0 Hz, 4.91 ppm(1H, ddd, J=9.0 Hz, 8.5 Hz, 6.4 Hz), 5.04 ppm(2H, s, 5.09 ppm(1H, d, J=1.0 Hz), 5.09 ppm(1H, d, J=12.5 Hz), 5.16 ppm(1H, d, J=12.5 Hz), 6.72 ppm(1H, d, J=8.3 Hz), 6.85 ppm(1H, d, J=7.8 Hz), 7.20–7.37 ppm(13H, m).

Compound 22:

Molecular formula: C$_{34}$H$_{44}$ClN$_3$O$_4$S$_3$; $^1$H-NMR(CDCl$_3$): 0.90 ppm(3H, t, J=7.1 Hz), 1.28 ppm(3H, s) 1.31 ppm(3H, s), 1.34–1.38 ppm(4H, m), 1.52 ppm(3H, s), 1.59–1.63 ppm(2H, m), 2.58 ppm(3H, s), 2.85 ppm(1H, dd, J=11.7 Hz, 4.6 Hz ), 2.89 ppm(1H, m), 3.00 ppm(1H, m), 3.10 ppm(1H, dd, J=11.7 Hz, 7.0 Hz), 3.10 ppm(1H, d, J=11.5 Hz), 3.13 ppm(1H, dd, J=11.2 Hz, 7.8 Hz), 3.35 ppm(1H, ddd, J=7.0 Hz, 6.6 Hz, 4.6 Hz), 3.44 ppm(1H, dd, J=11.2 Hz, 8.8 Hz), 3.49 ppm(1H, d, J=6.6 Hz), 3.59 ppm(1H, d, J=11.5 Hz), 4.16 ppm(1H, d, J=9.3 Hz ), 4.36 ppm(1H, br), 4.75 ppm (1H, ddd, J=9.3 Hz, 8.8 Hz, 7.8 Hz), 5.14 ppm(1H, d, J=12.5 Hz), 5.20 ppm(1H, d, J=12.5 Hz), 6.70 ppm(1H, dd, J=7.6 Hz, 1.2 Hz), 6.85 ppm(1H, dd, J=7.3 Hz, 1.2 Hz), 7.20 ppm(1H, dd, J=7.6 Hz, 7.3 Hz), 7.29 ppm(2H, d, J=8.8 Hz), 7.33 ppm(2H, d, J=8.8 Hz), 12.87 ppm(1H, br). $^{13}$C-NMR (CDCl$_3$): 14.05 ppm(q), 21.94 ppm(q), 22.49 ppm(t), 23.29 ppm(q), 26.02 ppm(q), 31.88 ppm(t), 32.19 ppm(t), 35.00 ppm(t), 35.44 ppm(t), 36.59 ppm(t), 41.20 ppm(t), 45.66 ppm(s), 45.86 ppm(q), 66.33 ppm(t), 72.96 ppm(d), 77.72 ppm(d), 78.08 ppm(d) 79.62 ppm(d), 83.67 ppm(s), 115.38 ppm(d), 116.25 ppm(s), 121.38 ppm(d), 128.82 ppm (d), 129.51 ppm(d), 132.16 ppm(d), 134.06 ppm(s), 134.33 ppm(s), 143.79 ppm(s), 159.73 ppm(s), 171.76 ppm(s), 172.85 ppm(s), 178.26 ppm (s).

Compound 23:

Molecular formula: C$_{41}$H$_{49}$Cl$_2$N$_3$O$_4$S$_3$; $^1$H-NMR (CDCl$_3$): 0.90 ppm(3H, t, J=7.1Hz), 1.29 ppm(3H, s), 1.32 ppm(3H, s), 1.34–1.40 ppm(4H, m), 1.50 ppm(3H, s), 1.60–1.66 ppm(2H, m), 2.58 ppm(3H, s), 2.91–3.07 ppm (4H, m), 3.08 ppm(2H, d, J=11.2 Hz), 3.16–3.22 ppm(2H, m), 3.35 ppm(1H, dd, J=11.4 Hz, 8.8 Hz), 3.61 ppm(1H, d, J=11.2 Hz), 3.75 ppm(1H, d, J=8.0 Hz), 4.11 ppm(1H, d, J=8.8 Hz), 4.56 ppm(1H, d, J=11.2 Hz), 4.75 ppm(1H, dt, J=8.3 Hz, 8.8 Hz), 5.09 ppm(1H, d, J=12.5 Hz), 5.14 ppm(1H, d, J=11.2 Hz), 5.17 ppm(1H, d, J=12.5 Hz), 6.70 ppm(1H, d, J=7.6 Hz), 6.84 ppm(1H, d, J=7.6 Hz), 7.21 ppm(1H, t, J=7.6 Hz), 7.25–7.36 ppm (8H, m), 13.62 ppm(1H, br).

Example 22

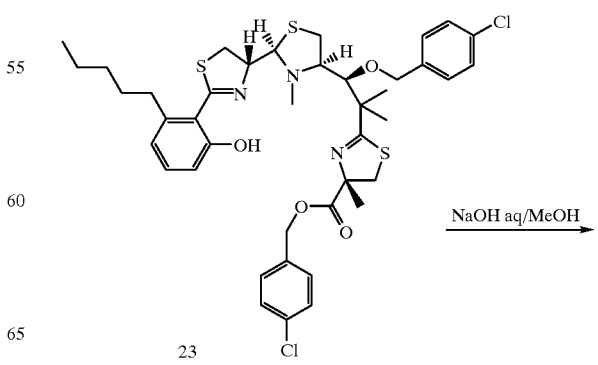

-continued

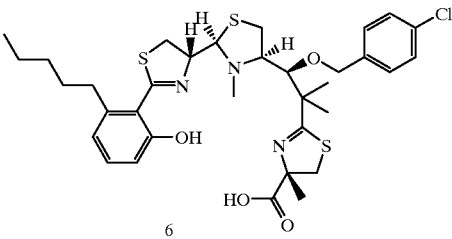
6

-continued

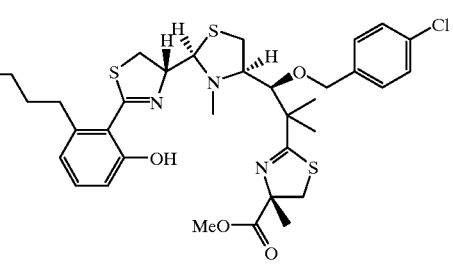
13

To a solution consisting of compound 23 (19. 6 mg) methanol (0.7 ml) and 1,4-dioxane (0. 2 ml) was added an aqueous solution of 1 N sodium hydroxide (50 μl), and the mixture was stirred for 24 hours. To the reaction mixture, dichloromethane was added, and the mixture was washed with an aqueous solution of 5% potassium hydrogen sulfate. The organic layer was dried over anhydrous sodium sulfate and the solvent was removed by evaporation in vacuo. The resultant residue was subjected to silica gel column chromatography(eluted consecutively with dichloromethane,1% methanol/dichloromethane and 3% methanol/dichloromethane) to give compound 6(14.6 mg).

Molecular formula: $C_{34}H_{44}ClN_3O_4S_3$; FAB MS m/z=690 [M+H]$^+$, 441,125; $^1$H-NMR(CDCl$_3$): 0.90ppm(3H, t, J=7.1Hz), 1.32 ppm(3H, s), 1.34 ppm(3H, s), 1.36–1.39 ppm(4H, m), 1.51 ppm(3H, s), 1.59–1.65 ppm(2H, m), 2.60 ppm(3H, s), 2.93–3.08 ppm(4H, m), 3.17–3.24 ppm(2H, m), 3.18 ppm(1H, d, J=11.7 Hz), 3.37 ppm(1H, dd, J=11.2 Hz, 8.5 Hz), 3.62 ppm(1H, d, J=11.7 Hz), 3.70 ppm(1H, d, J=8.1 Hz), 4.14 ppm(1H, d, J=8.5 Hz), 4.55 ppm(1H, d, J=11.2 Hz), 4.75 ppm(1H, q, J=8.5 Hz), 5.16 ppm(1H, d, J=11.2 Hz), 6.70 ppm(1H, dd, J=7.6 Hz, 1.3 Hz), 6.84 ppm(1H, dd, J=8.3 Hz, 1.3 Hz), 7.21 ppm (1H, dd, J=8.3 Hz, 7.6 Hz), 7.28 ppm(2H, d, J=8.8 Hz), 7.35 ppm(2H, d, J=8.8 Hz). $^{13}$C-NMR (CDCl$_3$): 14.06 ppm(q), 22.50 ppm(t), 22.56 ppm(q) 23.50 ppm(q), 26.24 ppm(q), 31.93 ppm(t), 32.35 ppm(t), 34.84 ppm(t), 34.93 ppm(t), 35.54 ppm(t), 40.69 ppm(t), 45.95 ppm(q), 46.58 ppm(s), 74.69 ppm(t), 74.79 ppm(d), 78.32 ppm(d), 79.03 ppm(d), 83.70 ppm(s), 88.34 ppm(d), 115.54 ppm(d), 115.97 ppm(s), 121.32 ppm(d), 128.35 ppm (d), 128.77 ppm(d), 132.21 ppm(d), 133.03 ppm(s), 137.21 ppm(s), 143.82 ppm(s), 160.44 ppm(s), 171.89 ppm(s), 175.17 ppm(s), 181.28 ppm (s).

Example 23

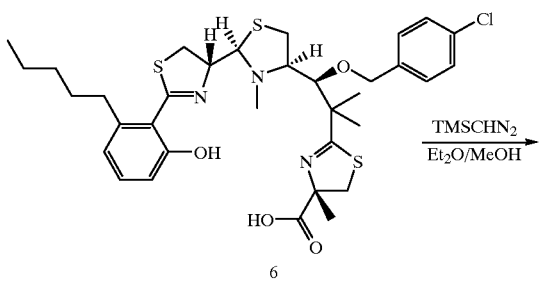
6

To a solution consisting of compound 6(12.5 mg), diethyl ether (0.4 ml) and methanol (0.4 ml) was added 0.2 M trimethylsilyldiazomethane/hexane solution (0.1 ml), and the mixture was stirred for 30 minutes at room temperature. The reaction mixture was diluted with ethyl acetate, washed consecutively with an aqueous solution of 5% potassium hydrogen sulfate and saturated saline. The organic layer was dried over anhydrous sodium sulfate and the solvent was removed by evaporation in vacuo. The residue was subjected to silica gel column chromatography (eluted consecutively with dichloromethane and 20%ethyl acetate/dichloromethane) and purified by using HPLC to give compound 13 (5.4 mg).

Molecular formula: $C_{35}H_{46}ClN_3O_4S_3$; $^1$H-NMR(CDCl$_3$): 0.90 ppm(3H, t, J=7.1 Hz), 1.32 ppm(3H, s), 1.35 ppm(3H, s), 1.35–1.47 ppm(4H, m), 1.50 ppm(3H, s), 1.60–1.66 ppm(2H, m), 2.60 ppm(3H, s), 2.91–3.05 ppm(3H, m), 3.10 ppm(1H, d, J=11.5 Hz), 3.11 ppm(1H, dd, J=11.5 Hz, 7.3 Hz), 3.19 ppm(1H, dd, J=11.2 Hz, 8.5 Hz), 3.21 ppm(1H, m), 3.38 ppm(1H, dd, J=11.2 Hz, 8.8 Hz), 3.66 ppm(1H, d, J=11.2 Hz), 3.74 ppm(3H, s), 3.76 ppm(1H, d, J=8.1 Hz), 4.13 ppm(1H, d, J=8.8 Hz), 4.59 ppm(1H, d, J=11.2 Hz), 4.77 ppm(1H, dt, J=8.5 Hz, 8.8 Hz), 5.17 ppm(1H, d, J=11.2 Hz), 6.70 ppm(1H, dd, J=7.6 Hz, 1.2 Hz), 6.84 ppm(1H, dd, J=8.3 Hz, 1.2 Hz), 7.21 ppm(1H, dd, J=8.3 Hz, 7.6 Hz), 7.28 ppm(2H, d, J=8.5 Hz), 7.37 ppm(2H, d, J=8.5 Hz), 13.58 ppm(1H, br). $^{13}$C-NMR(CDCl$_3$): 14.07 ppm(q), 21.99 ppm (q), 22.52 ppm(t), 23.39 ppm (q), 26.30 ppm(q), 31.94 ppm(t), 32.35 ppm(t), 34.90 ppm(t ), 34.90 ppm (t), 35.54 ppm(t), 41.42 ppm(t), 46.00 ppm(q), 46.48 ppm(s), 52.75 ppm (q), 74.49 ppm(t), 74.88 ppm(d), 78.24 ppm(d), 79.36 ppm(d), 83.98 ppm (s), 88.30 ppm(d), 115.52 ppm(d), 116.05 ppm(s), 121.23 ppm(d), 128.29 ppm(d), 128.79 ppm(d), 132.1 ppm(s), 132.88 ppm(d), 137.55 ppm (s), 143.80 ppm(s), 160.50 ppm(s), 171.63 ppm(s), 173.59 ppm (s), 178.81 ppm(s),

Example 24

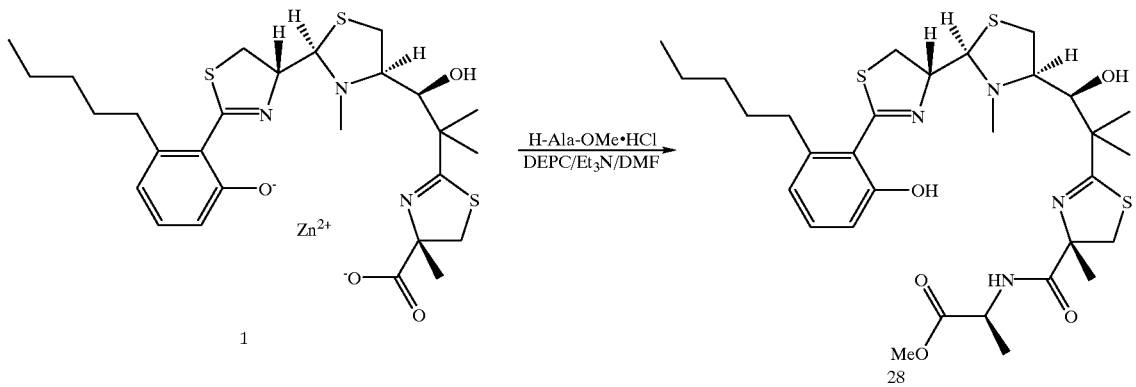

To a mixture of compound 1 (50 mg), L-alanine methylester hydrochloride (17 mg), triethylamine (17 μl), and dimethylformamide (0.4 ml), diethyl cyanophosphate (18 μl) was added at temperature, and the mixture was stirred for 25 hours. The reaction mixture was diluted with dichloromethane, and washed with an aqueous solution of 5% potassium hydrogen sulfate. The organic layer was dried over anhydrous sodium sulfate and the solvent was removed by evaporation in vacuo. The residue was purified by using silica gel column chromatography (eluted consecutively with dichloromethane, 20–50% ethyl acetate/hexane, ethyl acetate, and 10–20% methanol/ethyl acetate) to give compound 28 (34 mg).

Molecular formula: $C_{31}H_{46}N_4O_5S_3$; $^1$H-NMR(CDCl$_3$): 0.90 ppm(3H, t, J=7.1Hz), 1.32 ppm(3H, s) 1.35 ppm(3H, s), 1.35–1.39 ppm(4H, m), 1.40 ppm(3H, d, J=7.0 Hz), 1.50 ppm(3H, m), 1.59–1.63 ppm(2H, m), 2.66 ppm(3H, s), 2.84–3.04 ppm(3H, m), 3.14 ppm(1H, dd, J=11.5 Hz, 7.8 Hz), 3.17 ppm(1H, d, J=11.5 Hz), 3.23 ppm(1H, dd, J=11.5 Hz, 7.1 Hz), 3.41 ppm(1H, dt, J=7.1 Hz, 4.2 Hz), 3.47 ppm(1H, dd, J=11.5 Hz, 8.8 Hz), 3.54 ppm(1H, d, J=11.5 Hz), 3.60 ppm(1H, d, J=7.1 Hz), 3.72 ppm(3H, s), 4.20 ppm(1H, d, J=9.3 Hz), 4.54 ppm(1H, dq, J=7.6 Hz, 7.0 Hz), 4.75 ppm(1H, ddd, J=9.3 Hz, 8.8 Hz, 7.8 Hz), 6.70 ppm(1H, dd, J=7.6 Hz, 1.3 Hz), 6.84 ppm(1H, dd, J=8.3 Hz, 1.3 Hz), 7.21 ppm(1H, dd, J=8.3 Hz, 7.6 Hz), 7.43 ppm(1H, d, J=7.6 Hz)

Example 25

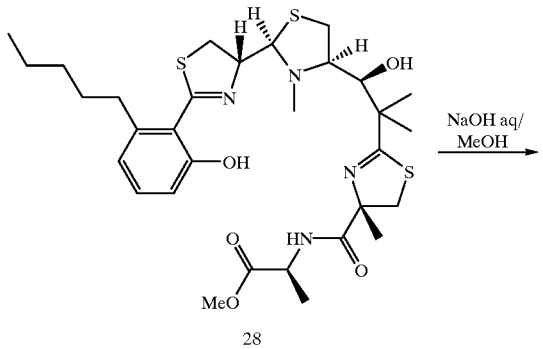

-continued

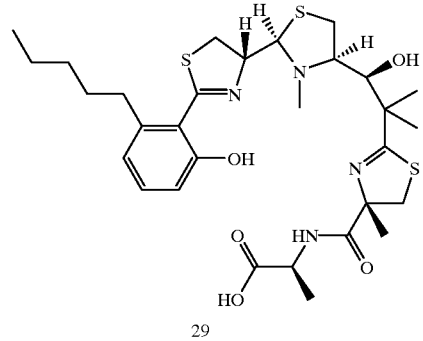

To compound 28 (21.5 mg) dissolved in methanol (1.7 ml), an aqueous solution (35 μl) of 1N sodium hydroxide was added with stirring at room temperature. After 24 hours, an aqueous solution (17 μl) of 1N sodium hydroxide was dropped into the mixture, and, after additional 24 hours, about ⅔ of methanol was removed by evaporation in vacuo. The residue was then acidified with an aqueous solution of 5% potassium hydrogen sulfate and extracted with dichloromethane. The organic layer was dried over anhydrous sodium sulfate, and the solvent was removed by evaporation in vacuo. The residue was subjected to silica gel column chromatography (eluted consecutively with 30–50% ethyl acetate/hexane, ethyl acetate, and 10% methanol/ethyl acetate) to give compound 29 (14.7 mg).

Molecular formula: $C_{30}H_{44}N_4O_5S_3$; $^1$H-NMR(CDCl$_3$): 0.90 ppm(3H, t, J=7.1 Hz), 1.29 ppm(3H, s) 1.31 ppm(3H, s), 1.33–1.37 ppm(4H, m), 1.42 ppm(3H, d, J=7.1 Hz), 1.54 ppm(3H, s), 1.59–1.63 ppm(2H, m), 2.61 ppm(3H, s), 2.86–3.01 ppm(3H, m), 3.15 ppm(1H, dd, J=11.5 Hz, 7.6 Hz), 3.15 ppm(1H, d, J=11.5 Hz), 3.25 ppm(1H, dd, J=11.5 Hz, 7.1 Hz), 3.44 ppm(1H, ddd, J=7.3 Hz, 7.1 Hz, 4.4 Hz), 3.48 ppm(1H, dd, J=11.5 Hz, 8.5 Hz), 3.59 ppm(1H, d, J=11.5 Hz), 3.61 ppm(1H, d, J=7.3 Hz), 4.18 ppm(1H, d, J=9.5 Hz), 4.73 ppm(1H, dq, J=7.5 Hz, 7.1 Hz), 4.73 ppm(1H, ddd, J=9.5 Hz, 8.5 Hz, 7.6 Hz), 6.72 ppm(1H, dd, J=7.6 Hz, 1.2 Hz), 6.85 ppm(1H, dd, J=8.3 Hz, 1.2 Hz), 7.22 ppm(1H, dd, J=8.3 Hz, 7.6 Hz), 7.55 ppm(1H, d, J=7.5 Hz). $^{13}$C-NMR(CDCl$_3$):14.05 ppm(q), 17.90 ppm(q), 22.49 ppm (t), 23.87 ppm (q), 24.29 ppm(q), 24.89 ppm(q), 31.87 ppm(t), 32.15 ppm(t), 35.12 ppm (t), 35.36 ppm(t), 36.64 ppm(t), 41.38 ppm(t), 45.54 ppm(s), 46.06 ppm (q), 48.14 ppm(s), 72.89 ppm(d), 77.93 ppm(d), 78.19 ppm(d), 79.30 ppm (d), 84.23 ppm(s), 115.60 ppm(d), 116.16 ppm(s), 121.58 ppm(d), 132.39 ppm(d), 143.83 ppm(s), 159.57 ppm(s), 172.50 ppm(s), 174.66 ppm (s), 174.96 ppm(s), 179.33 ppm(s).

Example 26

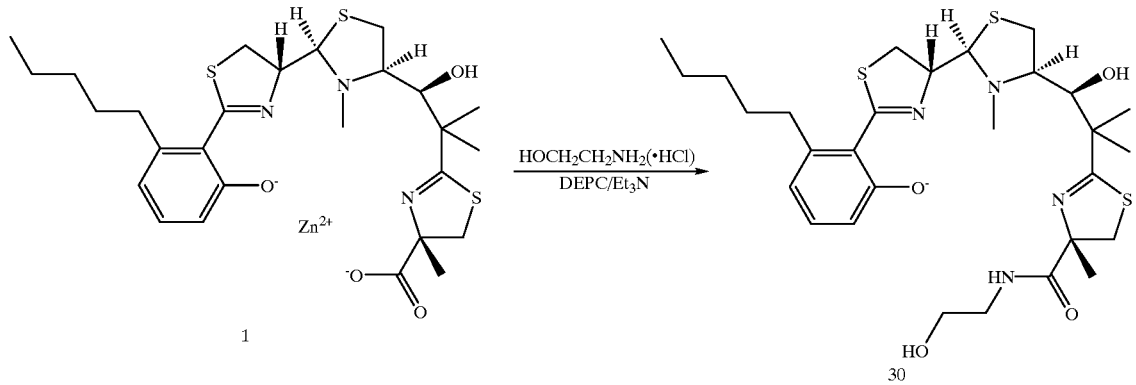

To a mixture of compound 1 (10 mg), ethanolamine hydrochloride (2.0 mg), triethylamine (5.0 μl), dimethylformamide (0.3 ml) and dichloromethane (0.1 ml), diethyl cyanophosphate (3.0 μl) was added at room temperature. After 24 hours, ethanol amine (2 μl) and diethyl cyanophosphate (3.0 μl) were added to the reaction. After 5 hours, ethanol amine (2 μl) and diethyl cyanophosphate (3.0 μl) were added to the mixture, and the mixture was stirred for 20 hours. The reaction mixture was diluted with ethyl acetate, and washed consecutively with an aqueous solution of 5% potassium hydrogen sulfate, an aqueous solution of saturated sodium hydrogen carbonate and saturated saline. The organic layer was dried over anhydrous sodium sulfate and the solvent was removed by evaporation in vacuo. The residue was purified with silica gel column chromatography (eluted consecutively with dichloromethane and 5% methanol/dichloromethane), and further purified by using HPLC to give compound 30 (4.5 mg).

Molecular formula: $C_{29}H_{44}N_4O_4S_3$; $^1$H-NMR(CDCl$_3$) :0.90 ppm(3H, t, J=7.1 Hz), 1.30 ppm(6H, s), 1.34–1.49 ppm(4H, m), 1.58 ppm(3H, s), 1.59–1.61 ppm(2H, m), 2.63 ppm(3H, s), 2.89–3.02 ppm(3H, m), 3.11 ppm(1H, d, J=11.7 Hz), 3.15 ppm(1H, dd, J=11.5 Hz, 7.3 Hz), 3.27 ppm(1H, dd, J=11.7 Hz, 7.3 Hz), 3.32–3.46 ppm(3H, m), 3.50 ppm(1H, dd, J=11.5 Hz, 8.5 Hz), 3.62–3.65 ppm(2H, m), 3.64 ppm (1H, d, J=11.7 Hz), 3.80 ppm(1H, d, J=7.6 Hz), 4.17 ppm(1H, d, J=9.8 Hz), 4.55 ppm(1H, br), 4.72 ppm(1H, ddd, J=9.8 Hz, 8.5 Hz, 7.3 Hz), 6.72 ppm(1H, dd, J=7.6 Hz, 1.3 Hz), 6.84 ppm(1H, dd, J=8.3 Hz, 1.3 Hz), 7.22 ppm(1H, dd, J=8.3 Hz, 7.6 Hz), 7.45 ppm(1H, br). $^{13}$C-NMR(CDCl$_3$) :14.05 ppm(q), 22.50 ppm(t), 22.92 ppm(q), 4.12 ppm (q), 25.11 ppm(q), 31.88 ppm(t), 32.20 ppm(t), 35.29 ppm(t, 35.40 ppm (t), 36.90 ppm(t), 41.90 ppm(t), 42.31 ppm(t), 45.36 ppm(s), 46.44 ppm (q), 62.27 ppm(t), 72.99 ppm(d), 77.94 ppm(d), 78.48pm (d), 79.39 ppm (d), 84.40 ppm(s), 115.40 ppm(d), 116.17 ppm(s), 121.57 ppm(d), 132.37 ppm (d), 143.86 ppm(s), 159.61 ppm(s), 172.28 ppm(s), 175.68 ppm (s), 180.23 ppm(s).

The compounds of the formula (I), which are obtained in the same manner as described in the examples stated above, are shown in Tables 3–7. The tables include the compounds obtained in the foregoing references and examples.

TABLE 3

| No. | $R^1$ | $R^2$ | $R^{3'}$ |
|---|---|---|---|
| 1 | COO$^-$ (Zn$^{2+}$) | — | H |
| 2 | COOH | H | H |
| 3 | COOH | H | Ac |
| 4 | COO$^-$ (Zn$^{2+}$) | — | Me |
| 5 | COOH | H | Me |
| 6 | COOH | H | CH$_2$ (4-ClC$_6$H$_4$) |
| 7 | COOH | Me | H |
| 8 | COOH | Ac | Ac |
| 9 | COONa | H | H |
| 10 | COOMe | Ac | Ac |
| 11 | COOMe | CH$_2$ (4-ClC$_6$H$_4$) | H |
| 12 | COOMe | H | H |
| 13 | COOMe | H | CH$_2$ (4-ClC$_6$H$_4$) |
| 14 | COOMe | Me | H |
| 15 | COOMe | Me | MTPA |
| 16 | COOMe | Me | =O |
| 17 | COOCH$_2$OMe | CH$_2$OMe | CH$_2$OMe |
| 18 | COOCH$_2$OMe | CH$_2$OMe | H |
| 19 | COOCH$_2$OMe | H | CH$_2$OMe |
| 20 | COOCH$_2$OMe | H | H |
| 21 | COOCH$_2$ (4-ClC$_6$H$_4$) | CH$_2$ (4-ClC$_6$H$_4$) | CH$_2$ (4-ClC$_6$H$_4$) |
| 22 | COOCH$_2$ (4-ClC$_6$H$_4$) | H | H |
| 23 | COOCH$_2$ (4-ClC$_6$H$_4$) | H | CH$_2$ (4-ClC$_6$H$_4$) |
| 24 | CONMeO$^-$ (Zn$^{2+}$) | — | H |
| 25 | CONMeOH | H | H |
| 26 | CONHMe | H | H |
| 27 | CONMe$_2$ | H | H |
| 28 | CONHCHMeCOOMe | H | H |
| 29 | CONHCHMeCOOH | H | H |
| 30 | CONHCH$_2$CH$_2$OH | H | H |
| 31 | CONH$_2$ | H | H |
| 32 | CH$_2$OH | H | H |
| 33 | CO—Cys—OH | H | H |
| 34 | CO—Cys—OMe | Me | H |
| 35 | CO—Gly—OH | H | H |
| 36 | CO—Gly—OH | H | Me |
| 37 | CO—Gly—OH | Me | H |
| 38 | CO—Gly—OMe | H | H |
| 39 | CO—Gly—OMe | H | Me |
| 40 | CO—Gly—OMe | Me | H |
| 41 | CO—Ser—OH | H | H |
| 42 | CO—Ser—OMe | H | H |
| 43 | CONH$_2$ | Et | H |

TABLE 4

| No. | R¹ | R² | R³' |
|---|---|---|---|
| 44 | CONH₂ | iPr | H |
| 45 | CONH₂ | Me | H |
| 46 | CONHCH₂CH₂NH₂ | H | H |
| 47 | CONHCH₂CH₂NHMe | H | H |
| 48 | CONHCH₂CH₂OMe | H | H |
| 49 | CONHCH₂CH₂SMe | H | H |
| 50 | CONHMe | CHF₂ | H |
| 51 | CONHMe | Et | H |
| 52 | CONHMe | Me | H |
| 53 | CONHMe | Pr | H |
| 54 | CONMeOEt | Et | H |
| 55 | CONMeOH | CHF₂ | H |
| 56 | CONMeOH | Et | H |
| 57 | CONMeOH | iPr | H |
| 58 | CONMeOH | Me | H |
| 59 | CONMeOMe | Me | H |
| 60 | CONMeOMe | Me | Me |
| 61 | COOCH₂ (2,3-Cl₂C₆H₃) | H | H |
| 62 | COOCH₂ (2,3-Cl₂C₆H₃) | H | Me |
| 63 | COOCH₂ (2,3-Cl₂C₆H₃) | Me | H |
| 64 | COOCH₂ (2,4-Cl₂C₆H₃) | H | H |
| 65 | COOCH₂ (2,4-Cl₂C₆H₃) | H | Me |
| 66 | COOCH₂ (2,4-Cl₂C₆H₃) | Me | H |
| 67 | COOCH₂ (2-ClC₆H₄) | H | H |
| 68 | COOCH₂ (3,4-Cl₂C₆H₂) | H | H |
| 69 | COOCH₂ (3-ClC₆H₄) | H | H |
| 70 | COOCH₂ (4-FC₆H₄) | H | H |
| 71 | COOCH₂ (4-FC₆H₄) | H | Me |
| 72 | COOCH₂ (4-FC₆H₄) | Me | H |
| 73 | COOCH₂ (4-MeC₆H₄) | H | H |
| 74 | COOCH₂ (4-MeC₆H₄) | H | Me |
| 75 | COOCH₂ (4-MeC₆H₄) | Me | H |
| 76 | COOCH₂CH₂F | H | H |
| 77 | COOCH₂CH₂F | H | Me |
| 78 | COOCH₂CH₂F | Me | H |
| 79 | COOCH₂OMe | H | Me |
| 80 | COOCH₂OMe | Me | H |
| 81 | COOCH₂Ph | H | H |
| 82 | COOCH₃Ph | H | Me |
| 83 | COOCH₂Ph | Me | H |
| 84 | COOCH₂SMe | H | H |

TABLE 5

| No. | R¹ | R² | R³' |
|---|---|---|---|
| 85 | COOCH₂SMe | H | Me |
| 86 | COOCH₂SMe | Me | H |
| 87 | COOCHF₂ | CHF₂ | H |
| 88 | COOEt | CHF₂ | Me |
| 89 | COOEt | Et | Et |
| 90 | COOEt | Et | H |
| 91 | COOEt | H | H |
| 92 | COOEt | H | Me |
| 93 | COOEt | Me | H |
| 94 | COOH | CH₂ (2-ClC₆H₄) | H |
| 95 | COOH | CH₂ (3,4-Cl₂C₆H₃) | H |
| 96 | COOH | CH₂ (3-ClC₆H₄) | H |
| 97 | COOH | CH₂ (4-MeC₆H₄) | H |
| 98 | COOH | CH₂ (4-MeC₆H₄) | Me |
| 99 | COOH | CH₂CH₂F | H |
| 100 | COOH | CH₂CH₂F | Me |
| 101 | COOH | CH₂OEt | H |
| 102 | COOH | CH₂OMe | H |
| 103 | COOH | CH₂Ph | H |
| 104 | COOH | CH₂Ph | Me |
| 105 | COOH | CHF₂ | Ac |
| 106 | COOH | CHF₂ | COCF₃ |
| 107 | COOH | CHF₂ | COEt |
| 108 | COOH | CHF₂ | COiPr |
| 109 | COOH | CHF₂ | COPh |
| 110 | COOH | CHF₂ | COPr |
| 111 | COOH | CHF₂ | Et |
| 112 | COOH | CHF₂ | H |

TABLE 5-continued

| No. | R¹ | R² | R³' |
|---|---|---|---|
| 113 | COOH | CHF₂ | iPr |
| 114 | COOH | CHF₂ | Me |
| 115 | COOH | CHF₂ | Pr |
| 116 | COOH | COEt | COEt |
| 117 | COOH | COEt | H |
| 118 | COOH | COiPr | COiPr |
| 119 | COOH | COiPr | H |
| 120 | COOH | CONHMe | H |
| 121 | COOH | CONHMe | Me |
| 122 | COOH | COOCH₂Ph | H |
| 123 | COOH | COOCH₂Ph | Me |
| 124 | COOH | COOEt | H |
| 125 | COOH | COOEt | Me |

TABLE 6

| No. | R¹ | R² | R³' |
|---|---|---|---|
| 126 | COOH | COOMe | H |
| 127 | COOH | COOMe | Me |
| 128 | COOH | COPh | COPh |
| 129 | COOH | COPh | H |
| 130 | COOH | Et | H |
| 131 | COOH | Et | Me |
| 132 | COOH | H | =O |
| 133 | COOH | H | CH₂ (2-ClC₆H₄) |
| 134 | COOH | H | CH₂ (3-ClC₆H₄) |
| 135 | COOH | H | CH₂ (4-MeC₆H₄) |
| 136 | COOH | H | CH₂CH₂F |
| 137 | COOH | H | CH₂Ph |
| 138 | COOH | H | COBu |
| 139 | COOH | H | COCF₃ |
| 140 | COOH | H | COEt |
| 141 | COOH | H | COiPr |
| 142 | COOH | H | CONHMe |
| 143 | COOH | H | COOCH₂Ph |
| 144 | COOH | H | COOEt |
| 145 | COOH | H | COOMe |
| 146 | COOH | H | COPh |
| 147 | COOH | H | COPr |
| 148 | COOH | H | Et |
| 149 | COOH | H | iPr |
| 150 | COOH | H | Pr |
| 151 | COOH | iPr | H |
| 152 | COOH | iPr | Me |
| 153 | COOH | Me | Ac |
| 154 | COOH | Me | CH₂ (4-MeC₆H₄) |
| 155 | COOH | Me | CH₂CH₂F |
| 156 | COOH | Me | CH₂Ph |
| 157 | COOH | Me | COCF₃ |
| 158 | COOH | Me | COEt |
| 159 | COOH | Me | COiPr |
| 160 | COOH | Me | CONHMe |
| 161 | COOH | Me | COOCH₂Ph |
| 162 | COOH | Me | COOEt |
| 163 | COOH | Me | COOMe |
| 164 | COOH | Me | COPh |
| 165 | COOH | Me | COPr |
| 166 | COOH | Me | Et |
| 167 | COOH | Me | iPr |
| 168 | COOH | Me | Me |
| 169 | COOH | Pr | H |

TABLE 7

| No. | R¹ | R² | R³' |
|---|---|---|---|
| 170 | COOiPr | H | H |
| 171 | COOiPr | H | Me |
| 172 | COOiPr | iPr | H |
| 173 | COOiPr | Me | H |
| 174 | COOMe | CH₂ (4-MeC₆H₄) | H |
| 175 | COOMe | CH₂CH₂F | H |
| 176 | COOMe | CH₂Ph | H |

TABLE 7-continued

| No. | R¹ | R² | R³' |
|---|---|---|---|
| 177 | COOMe | COCF₂ | COCF₃ |
| 178 | COOMe | COEt | COEt |
| 179 | COOMe | CONHMe | H |
| 180 | COOMe | CONHMe | Me |
| 181 | COOMe | COOCH₂Ph | H |
| 182 | COOMe | COOCH₂Ph | Me |
| 183 | COOMe | COOEt | H |
| 184 | COOMe | COOEt | Me |
| 185 | COOMe | COOMe | H |
| 186 | COOMe | COOMe | Me |
| 187 | COOMe | COPh | COPh |
| 188 | COOMe | Et | H |
| 189 | COOMe | H | CH₂ (3,4-Cl₂C₆H₃) |
| 190 | COOMe | H | CH₂ (4-MeC₆H₄) |
| 191 | COOMe | H | CH₂CH₂F |
| 192 | COOMe | H | CH₂Ph |
| 193 | COOMe | H | CONHMe |
| 194 | COOMe | H | COOCH₂Ph |
| 195 | COOMe | H | COOEt |
| 196 | COOMe | H | COOMe |
| 197 | COOMe | H | Et |
| 198 | COOMe | H | iPr |
| 199 | COOMe | iPr | H |
| 200 | COOMe | Me | CH₂OMe |
| 201 | COOMe | Me | CONHMe |
| 202 | COOMe | Me | COOCH₂Ph |
| 203 | COOMe | Me | COOEt |
| 204 | COOMe | Me | COOMe |
| 205 | COOMe | Me | Me |

EXPERIMENT

1. Antibacterial Activities (1) Methods

For bacteria, minimum Inhibitory Concentration (MIC, μg/mL) was determined using the agar dilution method designated by the Society for Chemotherapy in Japan. For Mycoplasma, the liquid dilution method was used for determining MIC. Serpulina and Clostridium among the bacteria tested were anaerobically cultured using Gas-pack method. Determination of MIC was conducted using the media having the following compositions depending on the bacteria tested.

PPLO medium (Difco) containing 12% horse serum and 1% glucose was used for Mycoplasma (M.) gallisepticum; a medium consisting of Hanks solution with 0.5% lactalbumin, 10% horse serum, 5% of 25% yeast extract, and 1% glucose for $M.$ hyopneumoniae; and PPLO medium (Difco) containing 20% horse serum, 10% of 25% yeast extract, and 1% glucose for $M.$ pneumoniae. Those media also contained 0.025% phenol red in order to enabling to detect the growth of the bacteria according to color changes. MIC values were determined after culturing at 37° C. for 120–168 hours.

Anaerobic culture was performed using Gas-pack method with Trypticase Soy agar (TSA, BBL) containing 5% defibrinated sheep blood for Serpulina hyodysenteriae, and with GAM medium (Nissui) for Clostridium perfringens. After culturing Serpulina hyodysenteriae at 37° C. for 96–120 hours and Clostridium perfringens at 37° C. for 24 hours, MICs were determined.

Antibacterial activities for Branhamella catarrhalis were determined according to the method of determining Minimum Growth Inhibitory Concentration designated by the Society for Chemotherapy in Japan. Thus, sensitivity-disc medium (Nissui) was used as a sensitivity determination medium, to which about 1 μl of $10^6$ CFU/ml of the bacterial suspension was inoculated.

Other bacteria were cultured at 37° C. for 20–24 hours using MHA for a determination medium before determination of MIC.

(2) Results

The antibacterial activities of the compounds tested was shown in Table 8.

Especially, low MICs of compounds 7, 8, 12, 18, 20 and 28 to Mycopasmas were obserbed.

In addition, compounds 7, 18 and 20 showed the activity to Serpulina (Treponema) hyodysenteriae and Clostridium perflingens as well.

TABLE 8

| | In vitro determination results (MIC: μg/ml) | | | | |
|---|---|---|---|---|---|
| | Mycoplasma | | | | |
| No. | Mp Mac (human) | Mg S6 (avian) | Mh ST-11 (swine) | Antibacterial activities to other bacteria | |
| 7 | 0.1 | 1.56 | 0.1 | S. hyodysenteriae ATCC 27164 | 1.56 |
| | | | | S. aureus FDA 209P | 1.56 |
| | | | | C. perfringens ATCC 13124 | 0.1 |
| 9 | 0.00625 | 0.2 | 0.025 | B. catarrhalis A 25238 | 3.13 |
| | | | | C. trachmatis D/UW-3/CX | 16 |
| | | | | E. avium A 14025 | 1.56 (50) |
| 12 | ≦0.00625 | 0.2 | ≦0.025 | | |
| 18 | 0.025 | 1.56 | 0.05 | | |
| 19 | 0.39 | 6.25 | 1.56 | | |
| 20 | ≦0.00625 | 0.1 | 0.025 | S. hyodysenteriae ATCC 27164 | 1.56 |
| | | | | C. perfringens ATCC 13124 | 3.13 |
| 22 | 0.39 | >3.13 | 0.1 | | |
| 24 | 0.025 | 0.39 | 0.1 | | |
| 26 | 0.78 | 6.25 | 6.25 | | |
| 27 | 0.78 | 6.25 | 6.25 | | |
| 28 | 0.05 | 0.39 | 0.1 | | |
| 30 | 0.2 | 0.78 | 0.39 | | |
| 31 | 0.2 | 0.39 | 0.2 | | |
| 32 | 0.025 | 0.39 | 0.05 | | |

Mp:M. pneumoniae, Mg: M. gallisepticum, Mh: M. hypneumoniae

2. In vivo Evaluation Test of Compound 9 for *M. gallisepticum*

(1) Methods

Eight-day old chickens (layer type, 6 chickens/group) were inoculated with $2.5 \times 10^2$ CFU of *M. gallisepticum* (field-isolated, macrolide resistant strain) per chicken in their right air sacs, and immediately after inoculation, they forcibly received a single dose of 25, 50, 100 mg/kg of compound 9.

Autopsy of the chickens was performed on 7th day after infection and the antibacterial effect was determined according to the incidence of the air-sac lesions and severity thereof.

Chlortetracycline formulation to be used only for animals was used as a control agent. The compounds and control agent were used after dissolved in 3% arabic gum.

(2) Results

As shown in Table 9, the administration of the compound resulted in the decrease in the number of chickens having air-sac lesions, which confirmed effectiveness of the compound.

TABLE 9

| Compound No. or Drug Name | Dose (mg × times) | Administration method | The number of chickens tested | The number of chickens having lesions | air-sac lesions (the number of chickens)** |  |  |
|---|---|---|---|---|---|---|---|
|  |  |  |  |  | (−) | (+) | (++−+++) |
| 9 | 25 × 1 | Orally | 6 | 2 | 4 | 0 | 2 |
|  | 50 × 1 | Orally | 6 | 2 | 4 | 1 | 1 |
|  | 100 × 1 | Orally | 6 | 1 | 5 | 0 | 1 |
| CTC* | 50 × 1 | Orally | 6 | 3 | 3 | 0 | 3 |
|  | 100 × 1 | Orally | 6 | 1 | 5 | 0 | 1 |
|  | 200 × 1 | Orally | 6 | 1 | 5 | 0 | 1 |
| Infected, not-administered control |  |  | 6 | 6 | 0 | 4 | 2 |
| Not-infected, not-administered control |  |  | 6 | 0 | 6 | 0 | 0 |

*CTC: chlortetracycline
**(−): non, (+): slight, (++)−(+++): moderate to severe.

3. Antifungal Activities

Method:

Antifungal activities of the compounds to *Candida albicans* (strain Ca-15) and *Asperilhm fumigatus* (strain MA), representative pathogenic fungi, were determined by microliquid dilution method using 96-well microplates. A fungal suspension stored under freezing was adjusted to $1 \times 1 0^5 CFU/ml$ by medium, of which 100 µl portions were charged into each well. The compound of the present invention was dissolved in dimethylsulfoxide (DMSO). Using the resultant solution, 2-fold dilution series were prepared together with the fungal suspension charged into the wells. YNB medium and RPMI medium were used. After cultured for 24 hours at 30° C., evaluation was performed by detecting the turbidity (wave length: 595 nm) using microplate reader.

(2) Results

TABLE 10

| | Antifungal activities: $IC_{50}$ (µg/ml) | | | |
|---|---|---|---|---|
| | *Candida albicans* | | *Aspergillus fumigatus* | |
| Compound No. | YNB | RPMI | YNB | RPMI |
| 2 | 6.3 | 1.6 | 3.2 | 0.2 |
| 9 | 6.3 | 1.6 | 3.2 | 0.2 |
| 20 | >100 | 3.2 | >100 | >100 |
| 25 | 50 | 6.3 | 50 | 0.2 |

Strong antifungal activities of the compounds stated above were observed in vitro.

4. Growth Inhibition Activities to Avian Coccidial Protozoa

The kidneys of SPF new born chicken was sterilely removed, which was treated with trypsin and the resultant primary kidney cells were cultured in 24-well plate. Monolayer culture after cultured for 3 days was treated simultaneously with compounds adjusted to predetermined concentration and sporozoit obtained by artificial excystation, which was cultured a 40° C. Premature and mature schizonts were observed under microscope, and the growth inhibition activities (suppression rate) for each treatment group were calculated at a proportion of the number of schizonts for the sporozoit-inoculated, compound-untreated control group (100%). As shown in Table 11, out of several compounds which showed said activities, compounds 7 and 19 especially showed strong growth inhibition activities. Concentrations showing growth inhibition effects was 156 µg/ml. The compounds did not show any cytotoxicity to the primary kidney culture cells at the same concentration.

TABLE 11

| In vitro growth inhibition activities* to an avian coccidium, *Eimeria tenella* | | |
|---|---|---|
| Compound No. | Effective dose (µg/ml) | Cytotoxicity (µg/ml) |
| 2 | 2.5 | 10 |
| 3 | 10 | >10 |
| 7 | 0.156 | 10 |
| 10 | >10 | >10 |

TABLE 11-continued

In vitro growth inhibition activities* to an avian coccidium, *Eimeria tenella*

| Compound No. | Effective dose (µg/ml) | Cytotoxicity (µg/ml) |
|---|---|---|
| 11 | 10 | >10 |
| 12 | 0.625 | >10 |
| 13 | >10 | >10 |
| 18 | 10 | >10 |
| 19 | 0.156 | 10 |
| 20 | 0.625 | >10 |
| 21 | >10 | >10 |
| 22 | 2.5 | >10 |
| 28 | 10 | >10 |
| 30 | 2.5 | >10 |
| 31 | — | 10 |
| 32 | 10 | >10 |

*Growth inhibition activities: regarded more than 80% of suppression rate as effective.

5. Effect of Suppression of Reaction to Mitogen of Mice Kidney Cells, in vitro

To each well of 96 well microtiter plate were added $5 \times 10^5$ spleen cells of BDF1 mice suspended in 0.1 ml of RPMI 1640 medium supplemented with 10% bovine fetus serum (supplemented with 2 mM sodium hydrogen carbonate, 50 Units/ml of penicillin, 50 µg/ml of streptomycin, and $5 \times 10^{-5}$M of 2-mercaptoethanol), and then, 5 µg/ml of Concanavalin A (Con A) or 10 µg/ml of lypopolysaccaride (LPS) and various concentrations of test substance, of which final volume was adjusted to 0.2 ml. Test substances were dissolved in dimethylsulfoxide (DMSO), diluted with RPMI 1640 stated above, and added to the wells so that final concentration of the substances becomes less than 10000 ng/ml. The 96-well microtiter plates were cultured at 37° C. for 3 days in an incubator which was maintained at the humidity of 100%, 5% of carbon dioxide and 95% of air. After cultivation is completed, 25 ml of 6 mg/ml solution of MTT {3-(4,5-dimethylthiazol-2yl)-2,5 diphenyltetrazoliumbromide} (Sigma) is added to each well, which is cultured at 37° C. for 4 days under the same conditions. After cultivation is completed, formazan formed is dissolved by adding 50 µl of a solution of 20% dodecyl sodium sulfonate (SDS) in 0.02N hydrochloric acid and kept standing at 37° C. for 24 hours. The absorbance (OD) of the formazan which was produced in proportion to the number of alive cells, was determined by using immunoreader equipped with 570 nm filter (see The Journal of Immunological Methods, Vol.65, 55–63, 1983).

Cell growth inhibition rate and $IC_{50}$ value were calculated according to the correlation between the concentration and the absorbance for each substance.

The results are given in Tables 12 and 13.

TABLE 12

Suppressive effects of the following compounds on the reaction to Concanavalin A of mice spleen cells

| Concentration of compound (ng/ml) | Suppression rate (%) | | | |
|---|---|---|---|---|
| | Compound 6 | Compound 7 | Compound 18 | Compound 20 |
| 39 | | 10.0 | 14.7 | |
| 78 | | 16.5 | 25.7 | |
| 156 | 0 | 60.7 | 75.5 | |
| 312 | 16.5 | 98.0 | 94.9 | 0 |
| 625 | 87.4 | 100.8 | 98.6 | 102.0 |
| 1250 | 98.6 | | | 101.0 |
| 2500 | 102.5 | | | 101.0 |
| $IC_{50}$ values | 399 | 129 | 101 | 506 |

TABLE 13

Suppressive effects of the following compounds on the reaction to lypopolusaccaride of mice spleen cells

| Concentration of compound (ng/ml) | Suppression rate (%) | | | |
|---|---|---|---|---|
| | Compound 6 | Compound 7 | Compound 18 | Compound 20 |
| 39 | | 17.2 | 27.4 | |
| 78 | | 42.5 | 41.5 | |
| 156 | 17.7 | 80.0 | 74.6 | |
| 312 | 24.4 | 98.6 | 93.4 | 2.1 |
| 625 | 84.3 | 102.4 | 100.6 | 98.8 |
| 1250 | 98.0 | | | 98.2 |
| 2500 | 104.7 | | | 96.3 |
| $IC_{50}$ values | 368 | 84 | 84 | 380 |

As shown in Tables 11 and 12, compounds 6, 7, 18 and 20 suppressed the reactions to Con A and LPS of spleen cells.

EFFECT OF THE INVENTION

The compound represented by the formula (I) of the present invention has especially anti-mycoplasma acitivity, antibacterial activities, antifungal activities and immunosuppressive activities and is useful as an anti-mycoplasma agent, antibacterial agent, antifungal agent and immunosuppressor.

We claim:

1. A compound represented by the formula (I):

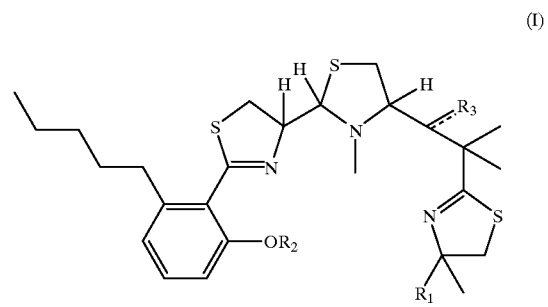

(I)

wherein $R^1$ is (1) $COOR^4$ wherein $R^4$ is hydrogen atom, optionally substituted alkyl, optionally substituted aralkyl, optionally substituted heteroaryl or optionally substituted heteroarylalkyl; (2) $CONR^5R^6$ wherein $R^5$ and $R^6$ are the same or different and represent hydrogen atom, hydroxyl, optionally substituted alkyl, optionally substituted alkoxyl, optionally substituted aryl, optionally substituted aralkyl, optionally substituted heteroaryl or optionally substituted heteroarylalkyl, provided that when one of $R^5$ and $R^6$ is hydroxyl or optionally substituted alkoxyl, the other is hydrogen atom, optionally substituted alkyl, optionally substituted aryl or optionally substituted aralkyl; (3) Co—$R^7$—OR wherein $R^7$ is α-amino acid residue and R is hydrogen atom or alkyl; or (4) $CH_2OR^8$ wherein $R^8$ is hydrogen atom, optionally substituted alkyl, optionally substituted aralkyl, optionally substituted heteroaryl, optionally substituted heteroarylalkyl, $COR^9$ wherein $R^9$ is hydrogen atom, optionally substituted alkyl, optionally substituted aryl, optionally substituted aralkyl, optionally substituted heteroaryl or optionally substituted heteroarylalkyl, $COOR^{10}$ wherein $R^{10}$ is optionally substituted alkyl, optionally substituted aryl, optionally substituted aralkyl, optionally substituted heteroaryl or optionally substituted heteroarylalkyl, or $CONR^{11}R^{12}$ wherein $R^{11}$ and $R^{12}$ are the same or different and represent hydrogen atom, optionally substituted alkyl, optionally substituted aryl, optionally substituted aralkyl, optionally substituted heteroaryl or optionally substituted heteroarylalkyl, $R^2$ is hydrogen atom, optionally substituted alkyl, optionally substituted aralkyl, optionally substituted heteroarylt optionally substituted heteroarylalkyl, $COR^{13}$ wherein $R^{13}$ is hydrogen atom, optionally substituted alkyl, optionally substituted aryl, optionally substituted aralkyl, optionally substituted heteroaryl or optionally substituted heteroarylalkyl, $COOR^{14}$ wherein $R^{14}$ is optionally substituted alkyl, optionally substituted aryl, optionally substituted aralkyl, optionally substituted heteroaryl or optionally substituted heteroarylalkyl, or $CONR^{15}R^{16}$ wherein $R^{15}$ and $R^{16}$ are the same or different and represent hydrogen atom, optionally substituted alkyl, optionally substituted aryl, optionally substituted aralkyl, optionally substituted heteroaryl or optionally substituted heteroarylalkyl; a broken line ( - - - ) represents the presence or absence of a double bond, provided that when it presents the presence of the double bond, $R^3$ is oxygen atom, or when it represents the absence of the double bond, $R^3$ is $OR^{3'}$ wherein $R^{3'}$ is hydrogen atom, optionally substituted alkyl, optionally substituted aralkyl, optionally substituted heteroaryl, optionally substituted heteroarylalkyl, $COR^{17}$ wherein $R^{17}$ is hydrogen atom, optionally substituted alkyl, optionally substituted aryl, optionally substituted aralkyl, optionally substituted heteroaryl or optionally substituted heteroarylalkylt $COOR^{18}$ wherein $R^{18}$ is optionally substituted alkyl, optionally substituted aryl, optionally substituted aralkyl, optionally substituted heteroaryl or optionally substituted heteroarylalkyl, or $CONR^{19}R^{20}$ wherein $R^{19}$ and $R^{20}$ are the same or different and represent hydrogen atom, optionally substituted alkyl, optionally substituted aryl, optionally substituted aralkyl, optionally substituted heteroaryl or optionally substituted heteroarylalkyl, or a salt or metal chelate thereof, provided that the metal chelate is excluded when $R^1$ is COOH, $R^2$ is hydrogen atom and $R^3$ is OH.

2. A compound of claim 1 wherein $R^1$ is $COOR^4$ wherein $R^4$ is hydrogen atom, optionally substituted alkyl or optionally substituted benzyl, or a salt or metal chelate thereof.

3. A compound of claim 1 wherein $R^1$ is $CONR^5R^6$, wherein $R^5$ and $R^6$ are the same or different and represent hydrogen atom, hydroxyl, alkoxyl, alkyl, carboxyalkyl, alkoxycarbonylalkyl or hydroxyalkyl, or a salt or metal chelate thereof.

4. A compound of claim 1 wherein $R^2$ is hydrogen atom, optionally substituted alkyl, optionally substituted benzyl or alkanoyl, or a salt or metal chelate thereof.

5. A compound of claim 1 wherein $R^3$ is $OR^{3'}$, wherein $R^{3'}$ is hydrogen atom, optionally substituted alkyl, optionally substituted benzyl or alkanoyl.

6. A medical drug comprising a compound of claim 1 or a salt or metal chelete thereof, as an effective ingredient.

7. An animal drug comprising a compound of claim 1 or a salt or metal chelete thereof, as an effective ingredient.

8. An anti-mycoplasma agent comprising a compound of claim 1 or a salt or metal chelete thereof, as an effective ingredient.

9. An anticoccidal agent comprising a compound of claim 1 or a salt or metal chelete thereof, as an effective ingredient.

10. An antibacterial agent comprising a compound of claim 1 or a salt or metal chelete thereof, as an effective ingredient.

11. An antifungal agent comprising a compound of claim 1 or a salt or metal chelete thereof, as an effective ingredient.

12. An immunosuppressor comprising a compound of claim 1 or a salt or metal chelete thereof, as an effective ingredient.

* * * * *